(12) United States Patent
Howell et al.

(10) Patent No.: US 7,677,723 B2
(45) Date of Patent: Mar. 16, 2010

(54) EYEGLASSES WITH A HEART RATE MONITOR

(75) Inventors: Thomas A. Howell, Palo Alto, CA (US); David Chao, Saratoga, CA (US); C. Douglass Thomas, Campbell, CA (US); Robert Grant Day, San Francisco, CA (US); Peter P. Tong, Mountain View, CA (US)

(73) Assignee: IpVenture, Inc., Los Altos, CA (US)

( * ) Notice: Subject to any disclaimer, the term of this patent is extended or adjusted under 35 U.S.C. 154(b) by 288 days.

(21) Appl. No.: 11/650,626

(22) Filed: Jan. 6, 2007

(65) Prior Publication Data
US 2007/0109491 A1 May 17, 2007

Related U.S. Application Data

(60) Provisional application No. 60/787,850, filed on Apr. 1, 2006, provisional application No. 60/846,150, filed on Sep. 20, 2006, provisional application No. 60/763,854, filed on Jan. 30, 2006.

(51) Int. Cl.
*G02C 1/00* (2006.01)

(52) U.S. Cl. .......................... 351/158; 351/41

(58) Field of Classification Search ............ 351/41, 351/136, 158; 607/9, 14, 18
See application file for complete search history.

(56) References Cited

U.S. PATENT DOCUMENTS

| | | | |
|---|---|---|---|
| 320,558 A | 6/1885 | Hull |
| 669,949 A | 3/1901 | Underwood |
| 1,255,265 A | 2/1918 | Zachara |
| 1,917,745 A | 7/1933 | Weiss |
| 2,249,572 A | 7/1941 | Lieber |
| 2,638,532 A | 5/1953 | Brady |
| 2,794,085 A | 5/1957 | De Angells |
| 2,818,511 A | 12/1957 | Ullery et al. |
| 2,830,132 A | 4/1958 | Borg |

(Continued)

FOREIGN PATENT DOCUMENTS

CN   88203065   11/1988

(Continued)

OTHER PUBLICATIONS

"±1.5g Dual Axis Micromachined Accelerometer", Freescale Semiconductor, Inc., Motorola Semiconductor Technical Data, MMA6260Q, 2004, pp. 1-7.

(Continued)

*Primary Examiner*—Huy K Mai

(57) ABSTRACT

A pair of glasses with a heart-rate monitor according to one embodiment. The heart-rate monitor is configured to measure the heart rate of the user of the glasses. The heart-rate monitor can include a sensor with a radiation transmitter and a radiation receiver. The radiation could be infrared radiation. In one approach, the receiver measures signals transmitted by the transmitter through a body part of the user to measure the user's heart rate. The sensor could be incorporated in a clip to clip onto the body part of the user, such as the ear lobe of the user. In another approach, the receiver measures signals transmitted by the transmitter and reflected by a body part of the user to measure the user's heart rate.

26 Claims, 9 Drawing Sheets

U.S. PATENT DOCUMENTS

| | | |
|---|---|---|
| 2,904,670 A | 9/1959 | Calmes |
| 3,060,308 A | 10/1962 | Fortuna |
| 3,597,054 A | 8/1971 | Winter |
| 3,710,115 A | 1/1973 | Jubb |
| 4,165,487 A | 8/1979 | Corderman |
| 4,254,451 A | 3/1981 | Cochran, Jr. |
| 4,283,127 A | 8/1981 | Rosenwinkel et al. |
| 4,322,585 A | 3/1982 | Liautaud |
| 4,348,664 A | 9/1982 | Boschetti et al. |
| 4,389,217 A | 6/1983 | Baughman et al. |
| 4,526,473 A | 7/1985 | Zahn, III |
| 4,535,244 A | 8/1985 | Burnham |
| 4,608,492 A | 8/1986 | Burnham |
| 4,683,587 A | 7/1987 | Silverman |
| 4,751,691 A | 6/1988 | Perera |
| 4,757,714 A | 7/1988 | Purdy et al. |
| 4,773,095 A | 9/1988 | Zwicker et al. |
| 4,806,011 A | 2/1989 | Bettinger |
| 4,822,160 A | 4/1989 | Tsai |
| 4,822,161 A | 4/1989 | Jimmy |
| 4,851,686 A | 7/1989 | Pearson |
| 4,942,629 A | 7/1990 | Stadlmann |
| 4,962,469 A | 10/1990 | Ono et al. |
| 4,985,632 A | 1/1991 | Bianco et al. |
| 5,008,548 A | 4/1991 | Gat |
| 5,020,150 A | 5/1991 | Shannon |
| 5,036,311 A | 7/1991 | Moran et al. |
| 5,050,150 A | 9/1991 | Ikeda |
| 5,093,576 A | 3/1992 | Edmond et al. |
| 5,148,023 A | 9/1992 | Hayashi et al. |
| 5,151,600 A | 9/1992 | Black |
| 5,161,250 A | 11/1992 | Ianna et al. |
| 5,172,256 A | 12/1992 | Sethofer et al. |
| 5,306,917 A | 4/1994 | Black et al. |
| 5,353,378 A | 10/1994 | Hoffman et al. |
| 5,359,370 A | 10/1994 | Mugnier |
| 5,367,345 A | 11/1994 | da Silva |
| 5,379,464 A | 1/1995 | Schleger et al. |
| 5,382,986 A | 1/1995 | Black et al. |
| 5,394,005 A | 2/1995 | Brown et al. |
| 5,452,480 A | 9/1995 | Ryden |
| 5,455,640 A | 10/1995 | Gertsikov |
| 5,457,751 A | 10/1995 | Such |
| 5,500,532 A | 3/1996 | Kozicki |
| D369,167 S | 4/1996 | Hanson et al. |
| 5,510,981 A | 4/1996 | Berger et al. |
| 5,513,384 A | 4/1996 | Brennan et al. |
| 5,533,130 A | 7/1996 | Staton |
| 5,581,090 A | 12/1996 | Goudjil |
| 5,585,871 A | 12/1996 | Linden |
| 5,589,398 A | 12/1996 | Krause et al. |
| 5,590,417 A | 12/1996 | Rydbeck |
| 5,608,808 A | 3/1997 | da Silva |
| 5,634,201 A | 5/1997 | Mooring |
| 5,673,692 A | 10/1997 | Schulze et al. |
| 5,686,727 A | 11/1997 | Reenstra et al. |
| 5,715,323 A | 2/1998 | Walker |
| 5,737,436 A | 4/1998 | Boyden et al. |
| 5,900,720 A | 5/1999 | Kallman et al. |
| 5,941,837 A | 8/1999 | Amano et al. |
| 5,946,071 A | 8/1999 | Feldman |
| 5,966,746 A | 10/1999 | Reedy et al. |
| 5,980,037 A | 11/1999 | Conway |
| 5,988,812 A | 11/1999 | Wingate |
| 5,992,996 A | 11/1999 | Sawyer |
| 5,995,592 A | 11/1999 | Shirai et al. |
| 6,010,216 A | 1/2000 | Jesiek |
| 6,013,919 A | 1/2000 | Schneider et al. |
| 6,028,627 A | 2/2000 | Helmsderfer |
| 6,046,455 A | 4/2000 | Ribi et al. |
| 6,060,321 A | 5/2000 | Hovorka |
| 6,061,580 A | 5/2000 | Altschul et al. |
| 6,091,546 A | 7/2000 | Spitzer |
| 6,091,832 A | 7/2000 | Shurman et al. |
| 6,115,177 A | 9/2000 | Vossler |
| 6,132,681 A | 10/2000 | Faran et al. |
| 6,154,552 A | 11/2000 | Koroljow et al. |
| 6,176,576 B1 | 1/2001 | Green et al. |
| 6,225,897 B1 | 5/2001 | Doyle et al. |
| 6,231,181 B1 | 5/2001 | Swab |
| 6,236,969 B1 | 5/2001 | Ruppert et al. |
| 6,243,578 B1 | 6/2001 | Koike |
| 6,259,367 B1 | 7/2001 | Klein |
| 6,270,466 B1 | 8/2001 | Weinstein et al. |
| 6,292,213 B1 | 9/2001 | Jones |
| 6,301,367 B1 | 10/2001 | Boyden et al. |
| 6,307,526 B1 | 10/2001 | Mann |
| 6,343,858 B1 | 2/2002 | Zelman |
| 6,349,001 B1 | 2/2002 | Spitzer |
| 6,349,422 B1 | 2/2002 | Schleger et al. |
| 6,409,338 B1 | 6/2002 | Jewell |
| 6,426,719 B1 | 7/2002 | Nagareda et al. |
| 6,431,705 B1 | 8/2002 | Linden |
| 6,478,736 B1 | 11/2002 | Mault |
| 6,506,142 B2 | 1/2003 | Itoh et al. |
| 6,513,532 B2 | 2/2003 | Mault et al. |
| 6,517,203 B1 | 2/2003 | Blum et al. |
| 6,539,336 B1 | 3/2003 | Vock et al. |
| 6,542,081 B2 * | 4/2003 | Torch ........................ 340/575 |
| 6,546,101 B1 | 4/2003 | Murray et al. |
| 6,554,763 B1 | 4/2003 | Amano et al. |
| 6,619,799 B1 | 9/2003 | Blum et al. |
| 6,629,076 B1 | 9/2003 | Haken |
| 6,721,962 B1 | 4/2004 | Polaire |
| 6,729,726 B2 | 5/2004 | Miller et al. |
| 6,736,759 B1 | 5/2004 | Stubbs et al. |
| 6,764,194 B1 | 7/2004 | Cooper |
| 6,792,401 B1 | 9/2004 | Nigro et al. |
| 6,912,386 B1 | 6/2005 | Himberg et al. |
| 6,929,365 B2 | 8/2005 | Swab et al. |
| 6,947,219 B1 | 9/2005 | Ou |
| 7,013,009 B2 | 3/2006 | Warren |
| 7,031,667 B2 | 4/2006 | Horiguchi |
| 7,059,717 B2 | 6/2006 | Bloch |
| 7,073,905 B2 | 7/2006 | Da Pra' |
| 7,192,136 B2 | 3/2007 | Howell et al. |
| 7,255,437 B2 | 8/2007 | Howell et al. |
| 7,265,358 B2 | 9/2007 | Fontaine |
| 7,274,292 B2 | 9/2007 | Velhal et al. |
| 7,312,699 B2 | 12/2007 | Chornenky |
| 7,331,666 B2 | 2/2008 | Swab et al. |
| 7,429,985 B2 | 9/2008 | Kimura et al. |
| 7,376,238 B1 | 5/2009 | Rivas et al. |
| 2001/0005230 A1 | 6/2001 | Ishikawa |
| 2002/0017997 A1 | 2/2002 | Felkowitz |
| 2002/0081982 A1 | 6/2002 | Schwartz et al. |
| 2002/0084990 A1 | 7/2002 | Peterson, III |
| 2002/0089639 A1 | 7/2002 | Starner et al. |
| 2002/0090103 A1 | 7/2002 | Calisto, Jr. |
| 2002/0098877 A1 | 7/2002 | Glezerman |
| 2002/0109600 A1 | 8/2002 | Mault et al. |
| 2002/0140899 A1 | 10/2002 | Blum et al. |
| 2002/0197961 A1 | 12/2002 | Warren |
| 2003/0018274 A1 * | 1/2003 | Takahashi et al. ........... 600/500 |
| 2003/0022690 A1 | 1/2003 | Beyda et al. |
| 2003/0032449 A1 | 2/2003 | Giobbi |
| 2003/0062046 A1 | 4/2003 | Weismann |
| 2003/0063591 A1 | 4/2003 | Leung et al. |
| 2003/0065257 A1 | 4/2003 | Mault et al. |
| 2003/0067585 A1 | 4/2003 | Miller et al. |
| 2003/0068057 A1 | 4/2003 | Miller et al. |
| 2003/0226978 A1 | 12/2003 | Ribi et al. |
| 2004/0000733 A1 | 1/2004 | Swab et al. |
| 2004/0063378 A1 | 4/2004 | Nelson |

| | | |
|---|---|---|
| 2004/0096078 A1 | 5/2004 | Lin |
| 2004/0150986 A1 | 8/2004 | Chang |
| 2004/0156012 A1 | 8/2004 | Jannard et al. |
| 2004/0157649 A1 | 8/2004 | Jannard et al. |
| 2004/0160571 A1 | 8/2004 | Jannard |
| 2004/0160572 A1 | 8/2004 | Jannard |
| 2004/0160573 A1 | 8/2004 | Jannard et al. |
| 2005/0067580 A1 | 3/2005 | Fontaine |
| 2005/0213026 A1 | 9/2005 | Da Pra' |
| 2005/0230596 A1 | 10/2005 | Howell et al. |
| 2005/0238194 A1* | 10/2005 | Chornenky ............... 381/381 |
| 2005/0248717 A1 | 11/2005 | Howell et al. |
| 2005/0248719 A1 | 11/2005 | Howell et al. |
| 2005/0264752 A1 | 12/2005 | Howell et al. |
| 2006/0001827 A1 | 1/2006 | Howell et al. |
| 2006/0003803 A1 | 1/2006 | Thomas et al. |
| 2006/0023158 A1 | 2/2006 | Howell et al. |
| 2006/0107822 A1 | 5/2006 | Bowen |
| 2007/0030442 A1 | 2/2007 | Howell et al. |
| 2007/0046887 A1 | 3/2007 | Howell et al. |
| 2007/0098192 A1 | 5/2007 | Sipkema |
| 2007/0186330 A1 | 8/2007 | Howell et al. |
| 2007/0208531 A1 | 9/2007 | Darley et al. |
| 2007/0270663 A1 | 11/2007 | Ng et al. |
| 2007/0271065 A1 | 11/2007 | Gupta et al. |
| 2007/0271116 A1 | 11/2007 | Wysocki et al. |
| 2007/0271387 A1 | 11/2007 | Lydon et al. |
| 2008/0068559 A1 | 3/2008 | Howell et al. |
| 2008/0132382 A1 | 6/2008 | Sturzer |
| 2008/0144854 A1* | 6/2008 | Abreu ............... 381/74 |
| 2008/0262392 A1 | 10/2008 | Ananny et al. |

FOREIGN PATENT DOCUMENTS

| | | |
|---|---|---|
| CN | 89214222.7 | 3/1990 |
| CN | 90208199.3 | 11/1990 |
| EP | 1134491 A2 | 9/2001 |
| FR | 2530039 A1 | 1/1984 |
| GB | 1467982 | 3/1977 |
| JP | 58-113912 | 7/1983 |
| JP | 58-113914 | 7/1983 |
| JP | 02-181722 | 7/1990 |
| JP | 09-017204 | 1/1997 |
| JP | 10-161072 | 6/1998 |
| JP | 2000-039595 | 2/2000 |
| JP | 2002 341059 A | 11/2002 |
| TW | 484711 | 6/2001 |
| WO | WO 97/12205 A1 | 4/1997 |
| WO | WO 99/50706 | 10/1999 |
| WO | WO 02/06881 A2 | 1/2002 |
| WO | WO 03/069394 A1 | 8/2003 |
| WO | WO 03/100368 A1 | 12/2003 |
| WO | WO 2004/012477 A2 | 2/2004 |
| WO | WO 2004/025554 A1 | 3/2004 |

OTHER PUBLICATIONS

"APA Announces Shipment of the SunUV™ Personal UV Monitor", Press Release, Nov. 7, 2003, pp. 1-3.
"Camera Specs Take Candid Snaps", BBC News, Sep. 18, 2003, pp. 1-3.
"Cardo Wireless Attaching Clips and Wearing Headset", Cardo Systems, Inc., http://www.cardowireless.com/clips.php, downloaded Nov. 27, 2004, pp. 1-3.
"Environmental Health Criteria 14: Ultraviolet Radiation", International Programme on Chemical Safety, World Health Organization Geneva, 1979 http://www.ichem.org., pp. 1-102.
"Eyetop, Product-Features", eyetop eyewear, eyetop belt worn, http://www.eyetop.net/products/eyetop/features.asp., downloaded Nov. 6, 2003, pp. 1-2.
"Exclusive Media Event Marks Debut of Oakley Thump: World's First Digital Audio Eyewear", Oakley Investor Relations, Press Release, Nov. 15, 2004, pp. 1-2.
"Heart Rate Monitors", http://www.healthgoods.com, downloaded Dec. 4, 2004.
"How is the UV Index Calculated", SunWise Program, U.S. Environmental Protection Agency, http://www.epa.gov/sunwise/uvcalc. html, downloaded Oct. 14, 2004, pp. 1-2.
"Industrial UV Measurements", APA Optics, Inc., http://www.apaoptics.com/uv/, downloaded Jul. 12, 2004, p. 1.
"Motorola and Oakley Introduce First Bluetooth Sunglasses-Cutting Edge RAZRWIre Line Offers Consumers On-The-Go Connections", Motorola Mediacenter-Press Release, Feb. 14, 2005, pp. 1-2.
"Oakley Thump: Sunglasses Meet MP3 Player", with Image, http://news.designtechnica.com/article4665.html, Jul. 13, 2004.
"Personal UV monitor," OptIcs.org, http://optics.org/articles/news/6/6/7/1 (downloaded Dec. 20, 2003), Jun. 9, 2000, pp. 1-2.
"SafeSun Personal Ultraviolet Light Meter", http://healthchecksystems.com/safesun.htm, downloaded Jul. 12, 2004, pp. 1-4.
"SafeSun Personal UV Meter", Introduction, Optlx Tech Inc., http://www.safesun.com, downloaded Feb. 5, 2004, pp. 1-2.
SafeSun Personal UV Meter, features, Optix Tech Inc., http://www.safesun.com/features.html, downloaded May 1, 2004, pp. 1-2.
"Sharper Image—The FM Pedometer", e-Corporate Gifts.com, http://www.e-corporategifts.com/sr353.html, downloaded Jan. 22, 2005, pp. 1-2.
"Sun UV™ Personal UV Monitor", APA Optics, Inc., http://www.apaoptics.com/sunuv/uvfacts.html, downloaded Dec. 20, 2003, pp. 1-3.
"Ultraviolet Light and Sunglasses", Oberon's Frequently Asked Questions, http://www.oberoncompany.com/OBEnglish/FAQUV. html, downloaded Feb. 5, 2004, pp. 1-2.
"Ultraviolet Light Sensor", Barrett & Associates Engineering, http://www.barrettengineering.com/project_uvs.htm, downloaded Feb. 5, 2004, pp. 1-3.
"Ultraviolet Radiation (UVR)", Forum North, Ontario Ministry of Labour, http://www3.mb.sympatico.ca/~ericc/ULTRAVIOLET%20RADIATION.htm, downloaded Feb. 5, 2004, pp. 1-6.
"What Are Gripples?", Gripping Eyewear, Inc., http://www.grippingeyewear.com/whatare.html, downloaded Nov. 2, 2005.
"With Racing Heart", Skaloud et al, GPS World, Oct. 1, 2001, http://www.gpsworld.com/gpsworld/content/printContentPopup.jsp?id=1805, pp. 1-5.
Abrisa Product Information: Cold Mirrors, Abrisa, date unknown, p. 1.
Abrisa Product Information: Commercial Hot Mirror, Abrisa, date unknown, p. 1.
Alps Spectable, Air Conduction Glass, Bone Conduction Glass, htt;://www.alps-Inter.com/spec.htm, downloaded Dec. 10, 2003, pp. 1-2.
Altimeter and Compass Watches, http://store.yahoo.com/snowshack/altimeter-watches.html, downloaded May 3, 2004, pp. 1-2.
Bone Conduction Headgear HG16 Series, "Voiceducer," http://www.ternco-j.co.jp/html/English/HG16.html, downloaded Dec. 10, 2003, pp. 1-3.
Carnoy, David, "The Ultimate MP3 Player for Athletes? Could be.", CNET Reviews, May 14, 2004, pp. 1-4.
Clifford, Michelle A., "Acccelerometers Jump into the Consumer Goods Marker", Sensors Online, http://www.sensorsmag.com, Aug. 2004.
Cool Last Minute Gift Ideas!, UltimateFatBurner Reviews and Articles, http://www.ultimatefatburner.com/gift-ideas.html, downloaded May 10, 2005, pp. 1-3.
Comfees.com, Adjustable Sports Band Style No. 1243, http://shop.store.yahoo.com/comfees/adsporbansty.html, downloaded Apr. 18, 2003, pp. 1-2.
Dixen, Brian, "ear-catching", Supertesten, Mobil, date unknown, pp. 37-41.
Global Solar UV Index, A Practical Guide, World Health Organization, 2002, pp. 1-28.
Grobert, Sam, "Digit-Sizing Your Computer Data", News Article, Sep. 2004 p. 1.

Life Monitor V1.1, Rhusoft Technologies Inc., http://www.rhusoft.com/lifemonitor/, Mar. 1, 2003, pp. 1-6.
Manes, Stephen, "Xtreme Cam", Forbes Magazine, Sep. 5, 2005, p. 96.
Mio, PhyslCal, http://www.gophysical.com/, downloaded Jan. 27, 2004, 5 pages.
Monitoring Athletes Performance—2002 Winter Olympic News from KSL, Jan. 23, 2002, http://2002.ksl.com/news-3885i.php, pp. 1-3.
Niwa, "UV Index Information", http://www.niwa.cri.nz/services/uvozone/uvi-info, downloaded Jul. 15, 2004, pp. 1-2.
Pärkkä, Juha, et al., "A Wireless Wellness Monitor for Personal Weight Management", VTT Information Technology, Tampere, Finland, date unknown, p. 1.
Pedometer, Model HJ-112, Omron Instruction Manual, Omron Healthcare, Inc., 2003, pp. 1-27.
PNY Announces Executive Attaché USB 2.0 Flash Drive and Pen Series, Press Release, PNY Technologies, Las Vegas, Jan. 8, 2004, pp. 1-2.
PNY Technologies, "Executive Attaché" http://www.pny.com/products/flash/execattache.asp downloaded Nov. 16, 2005.
Polar WM41 and 42 weight management monitor, http://www.simplysports/polar/weight_management/wm41-42.htm, downloaded Jan. 28, 2004, pp. 1-3.
Questions Answers, Pedometer.com, http:/www.pedometer.com, downloaded May 5, 2005.
RazrWire, Motorola, 2005, 1 page.
SafeSun Personal UV Meter, Scientific Data, Optix Tech Inc., http://www.safesun.com/scientific.html, downloaded May 1, 2003, pp. 1-3.
SafeSun Sensor, User's Manual, Optix Tech Inc., date unknown.
SafeSun, Personal UV Meter, "Technical Specifications", Optix Tech Inc., http://www.safesun.com/technical.html, downloaded Jul. 12, 2004, pp. 1-2.
SafeSun, Personal UV Meter, Experiments, Optix Tech Inc., http://www.safesun.com/experiments.html, downloaded Feb. 5, 2004, pp. 1-2.
Shades of Fun, Blinking Light Glasses, http://www.shadesoffun.com/Nov/Novpgs-14.html, downloaded Jul. 9, 2005, pp. 1-4.
SportLine Fitness Pedometer-Model 360, UltimateFatBurner Superstore, http://www.ultimatefatburner-store.com/ac_004.html, downloaded May 10, 2005, pp. 1-2.
Steele, Bonnie G. et al., "Bodies in motion: Monitoring daily activity and exercise with motion sensors in people with chronic pulmonary disease", VA Research & Development, Journal of Rehabilitation Research & Development, vol. 40, No. 5, Sep./Oct. 2003, Supplement 2, pp. 45-58.
Stevens, Kathy, "Should I Use a Pedometer When I Walk?", Healtheon/WebMD, Apr. 14, 2000.
Sundgot, Jørgen "2nd-gen Motorola Bluetooth headset", InfoSync World, Mar. 1, 2003, http://www.infosync.no/news/2002/n/2841.html, pp. 1-2.
SunSensors, Segan Industries, Inc., http://www.segan-ind.com/sunsensor.htm, downloaded Feb. 5, 2004, pp. 1-3.
SunUV™, Personal UV Monitor, APA Optics, Inc., http://www.apaoptics.com/sunuv/models.html, downloaded Dec. 20, 2003.
SunUV™, Personal UV Monitor User's Guide, APA Optics, Inc., 2003 pp. 1-52.
Talking Pedometer, Sportline, Inc., date unknown.
Top Silicon Pin Photodiode, PD93-21C, Technical Data Sheet, Everlight Electronics Co., Ltd., 2004, pp. 1-9.
UV Light Meter, UVA and UVB measurement, UV-340, Instruction Manual, Lutron, date unknown, pp. 1-5.
UV-Smart, UVA/B Monitor, Model EC-960-PW, Instruction Manual, Tanlta Corporation of America, Inc., downloaded Nov. 16, 2001.
Vitaminder Personal Carb Counter with Convenient Key Chain, date unknown, pp. 1-4.
Nellcor OxiMax, Sensor Selection Guide, Tyco Healthcare, copyright 2002 Tyco Healthcare, Oct. 2002, 12 pages.
NELLCOR™ Oximax Sensors™, Tyco Healthcare ECE, http://www.tycohealth-ece.com/index.php?folder=53&article=100, downloaded Nov. 29, 2006 pp. 1-5.
Principles of Pulse Oximetry Technology, copyright 2002 Oximeter.org, http://www.oximeter.org/pulseox/principles.htm, downloaded Jul. 18, 2006, pp. 1-3.

* cited by examiner

EYEGLASSES WITH A HEART RATE MONITOR

CROSS-REFERENCE TO RELATED APPLICATIONS

This application is related to U.S. patent application Ser. No. 11/183,256, filed Jul. 15, 2005, and entitled "EYEGLASSES WITH ELECTRICAL COMPONENTS," which is hereby incorporated herein by reference, which in turn is a continuation-in-part of U.S. patent application Ser. No. 10/964,011, filed Oct. 12, 2004, and entitled "TETHERED ELECTRICAL COMPONENTS FOR EYEGLASSES," which is hereby incorporated herein by reference, which in turn claims priority to each of: (i) U.S. Provisional Patent Application No. 60/509,631, filed Oct. 9, 2003, and entitled "TETHERED ELECTRICAL COMPONENTS FOR EYEGLASSES," which is hereby incorporated herein by reference; (ii) U.S. Provisional Patent Application No. 60/527,565, filed Dec. 6, 2003, and entitled "ADAPTABLE COMMUNICATION TECHNIQUES FOR ELECTRONIC DEVICES," which is hereby incorporated herein by reference; (iii) U.S. Provisional Patent Application No. 60/562,798, filed Apr. 15, 2004, entitled "EYEWEAR WITH ULTRAVIOLET DETECTION SYSTEM," and which is hereby incorporated herein by reference; (iv) U.S. Provisional Patent Application No. 60/583,169, filed Jun. 26, 2004, entitled "ELECTRICAL COMPONENTS FOR USE WITH EYEWEAR, AND METHODS THEREFOR," and which is hereby incorporated herein by reference; (v) U.S. Provisional Patent Application No. 60/592,045, filed Jul. 28, 2004, entitled "EYEGLASSES WITH A CLOCK OR OTHER ELECTRICAL COMPONENT," and which is hereby incorporated herein by reference; and (vi) U.S. Provisional Patent Application No. 60/605,191, filed Aug. 28, 2004, entitled "ELECTRICAL COMPONENTS FOR USE WITH EYEWEAR, AND METHODS THEREFOR," and which is hereby Incorporated herein by reference.

U.S. patent application Ser. No. 11/183,256 also claims priority to each of: (i) U.S. Provisional Patent Application No. 60/618,107, filed Oct. 12, 2004, and entitled "TETHERED ELECTRICAL COMPONENTS FOR EYEGLASSES," which is hereby incorporated herein by reference; (ii) U.S. Provisional Patent Application No. 60/620,238, filed Oct. 18, 2004, entitled "EYEGLASSES WITH HEARING ENHANCED AND OTHER AUDIO SIGNAL-GENERATING CAPABILITIES," and which is hereby incorporated herein by reference; (iii) U.S. Provisional Patent Application No. 60/647,836, filed Jan. 31, 2005, and entitled "EYEGLASSES WITH HEART RATE MONITOR," which is hereby incorporated herein by reference; and (iv) U.S. Provisional Patent Application No. 60/647,826, filed Jan. 31, 2005, and entitled "EYEWEAR WITH ELECTRICAL COMPONENTS," which is hereby incorporated herein by reference.

The application also claims priority to each of: (i) U.S. Provisional Patent Application No. 60/787,850, filed Apr. 1, 2006, and entitled "EYEGLASSES WITH A HEART RATE MONITOR," which is hereby incorporated herein by reference; (ii) U.S. Provisional Patent Application No. 60/846,150, filed Sep. 20, 2006, and entitled "EYEGLASSES WITH ACTIVITY MONITORING," which is hereby incorporated herein by reference; and (iii) U.S. Provisional Patent Application No. 60/763,854, filed Jan. 30, 2006, and entitled "HAT WITH A RADIATION SENSOR," which is hereby incorporated herein by reference.

In addition, this application is related to each of: (i) U.S. patent application Ser. No. 10/822,218, filed Apr. 12, 2004, and entitled "EYEGLASSES FOR WIRELESS COMMUNICATIONS," which is hereby incorporated herein by reference; (ii) U.S. patent application Ser. No. 10/964,011, filed Oct. 12, 2004, and entitled "TETHERED ELECTRICAL COMPONENTS FOR EYEGLASSES," which is hereby incorporated herein by reference; (iii) U.S. patent application Ser. No. 11/006,343, filed Dec. 7, 2004, and entitled "ADAPTABLE COMMUNICATION TECHNIQUES FOR ELECTRONIC DEVICES," which is hereby incorporated herein by reference; (iv) U.S. patent application Ser. No. 11/078,855, filed Mar. 11, 2005, and entitled "EYEWEAR WITH RADIATION DETECTION SYSTEM," which is hereby incorporated herein by reference; (v) U.S. patent application Ser. No. 11/078,857, filed Mar. 11, 2005, and entitled "RADIATION MONITORING SYSTEM," which is hereby incorporated herein by reference; (vi) U.S. patent application Ser. No. 11/183,269, filed Jul. 15, 2005, and entitled "EYEWEAR SUPPORTING AFTER-MARKET ELECTRICAL COMPONENTS," which is hereby incorporated herein by reference; (vii) U.S. patent application Ser. No. 11/183,283, filed Jul. 15, 2005, and entitled "EVENT EYEGLASSES," which is hereby incorporated herein by reference; (viii) U.S. patent application Ser. No. 11/183,262, filed Jul. 15, 2005, and entitled "EYEGLASSES WITH HEARING ENHANCED AND OTHER AUDIO SIGNAL-GENERATING CAPABILITIES," which is hereby incorporated herein by reference; (ix) U.S. patent application Ser. No. 11/183,263, filed Jul. 15, 2005, and entitled "EYEGLASSES WITH A CLOCK OR OTHER ELECTRICAL COMPONENT," which is hereby incorporated herein by reference; (x) U.S. patent application Ser. No. 11/183,276, filed Jul. 15, 2005, and entitled "EYEGLASSES WITH ACTIVITY MONITORING," which is hereby incorporated herein by reference; and (xi) U.S. Provisional Patent Application No. 11/580,222, filed Oct. 11, 2006, and entitled "EYEGLASSES SUPPORTING AFTER MARKET ELECTRICAL COMPONENTS," which is hereby incorporated herein by reference.

BACKGROUND OF THE INVENTION

There are various devices to measure heart rates. For example, one approach depends on wrapping a band across a person's chest. Electrodes in the band can sense the person's heart beat and wirelessly transmit the measured signals to a receiver. This approach can be quite inconvenient because the person has to wear a band across his chest in order to get the necessary measurements.

Another approach to measure heart beat is to clip an infrared sensor onto a person's finger. The sensor is connected to a machine through a wire. This approach is unsatisfactory if one intends to remain active, or to use one's hands while measurements are taken.

It should be apparent from the foregoing that there is still a need for an accurate heart rate monitor that is convenient to use for a person who may be in motion.

SUMMARY OF THE INVENTION

In one embodiment, the present invention provides a heart rate sensor attached to, integral with or tethered to a pair of glasses. When worn, the pair of glasses is in a stable position relative to the user. The glasses serve as a good platform for heart rate sensing.

In one embodiment, the sensor can be an infrared transmitter with an infrared detector on a clip. The clip could be tethered to a temple of the glasses. The user can attach the clip to her ear lobe to measure her heart rate. With the ear lobe being adjacent to the glasses, the length of the wire tethering the clip to the temple could be relatively short. A short wire is more convenient for the user than a long wire, particularly if the user has to move around. Also, the degree of movement of the clip relative to the ear lobe typically is less if the wire is short, which could lead to more accurate measurements.

In another embodiment, instead of a wire, the clip could be electrically coupled to the glasses through an adjustable mechanical arm, or a semi-rigid arm or cable. The mechanical arm or semi-rigid arm or cable could enhance the stability of the clip relative to the glasses.

In one embodiment, there could be an output device to provide outputs to the user, such as regarding her heart rate. For example, the output device could be based on audio or visual capabilities or both. In the embodiment with visual outputs, the output device could be located at the inside, peripheral position of the glasses, such as close to a hinge of the glasses, linking a temple to a lens holder.

In one embodiment, there could be a wireless transceiver in the glasses to send signals regarding the monitored heart rate to a portable or handheld device carried by the user for additional processing and/or display.

In another embodiment, signals regarding the monitored heart rate can be wirelessly received by a non-portable device, such as a stationary bike or a treadmill. The signals could be used to adjust the operations of the device, such as changing the speed of the treadmill based on the monitored heart rate.

In another embodiment, the glasses further include a memory device storing, for example, exercise programs or songs. The memory device could be integral with or attached to the glasses. The user could be following a stored workout program, which could give the user commands, such as, "Keep running at the same pace for the next 3 minutes"; or "Keep running at the same pace until I tell you to stop." At the end of the workout program, the user could be notified of the number of calories burned, distance traveled, etc.

In another embodiment, the heart rate monitor is for monitoring the user's certain health conditions, such as to help the user with irregular heart beat. For example, the glasses keep track of the user's heart rate, which could be subsequently downloaded to another device to be displayed for a doctor. In another example, if the monitored heart rate exceeds certain predetermined threshold, an alert signal would be automatically sent to a health care provider for the user.

In yet another embodiment, the heart rate sensor or monitor could be designed as an aftermarket product, such as designed in or designed to be attachable to a replaceable temple or replaceable temple tip. This allows the user to acquire the sensor or monitor subsequent to getting a pair of glasses.

In one embodiment, the glasses further include at least a portion of other electronic devices, such as a pedometer or a temperature sensor. The outputs from the different devices could be combined to help the user. For example, if the user constantly experiences irregular heart beat, the pedometer with the heart rate monitor would be able to better indicate if the user has been active or at rest at the onset of an irregular heart beat.

In one embodiment, the heart rate sensor is based on measuring reflected radiation. The sensor can be configured to maintain substantially a constant distance to the position on the skin that the sensor is measuring. Such a sensor could include an infrared transceiver. In one example, such a sensor is at a nose pad of a pair of glasses.

In different embodiments, the glasses could be sunglasses, prescription glasses, reading glasses, or swimming or skiing goggles. In one embodiment, there could be a strap, cord or lanyard attached to the glasses. In another embodiment, a heart rate monitor or sensor is attached or tethered to, or integral with, the strap, cord or lanyard. In one embodiment, a heart rate monitor or sensor is attached or tethered to, or integral with, an apparatus wearable to the head of the user. Examples of such an apparatus include hats, headbands and helmets.

Other aspects and advantages of the present invention will become apparent from the following detailed description, which, when taken in conjunction with the accompanying drawings, illustrates by way of example the principles of the invention.

Same numerals in FIGS. 1-7 are assigned to similar elements in all the figures. Embodiments of the invention are discussed below with reference to FIGS. 1-7. However, those skilled in the art will readily appreciate that the detailed description given herein with respect to these figures is for explanatory purposes as the invention extends beyond these limited embodiments.

DESCRIPTION OF THE INVENTION

In one embodiment, a pair of glasses for a user has a heart rate (heart beat) monitor. The heart rate monitor can be partially or fully embedded in the eyeglasses. For example, the heart rate monitor can be substantially embedded in a temple of the eyeglasses. In another embodiment, the heart rate monitor can be coupled (either permanently or temporarily) to the eyeglasses.

In one embodiment, the heart rate monitor can include an infrared sensor (or IR sensor) and processing circuitry. Using measurements from the infrared sensor, the processing circuitry can determine the user's heart rate. The eyeglasses can also include one or more output devices, such as a speaker or beeper, for audio output, and/or a display for visual output.

Figure 1:
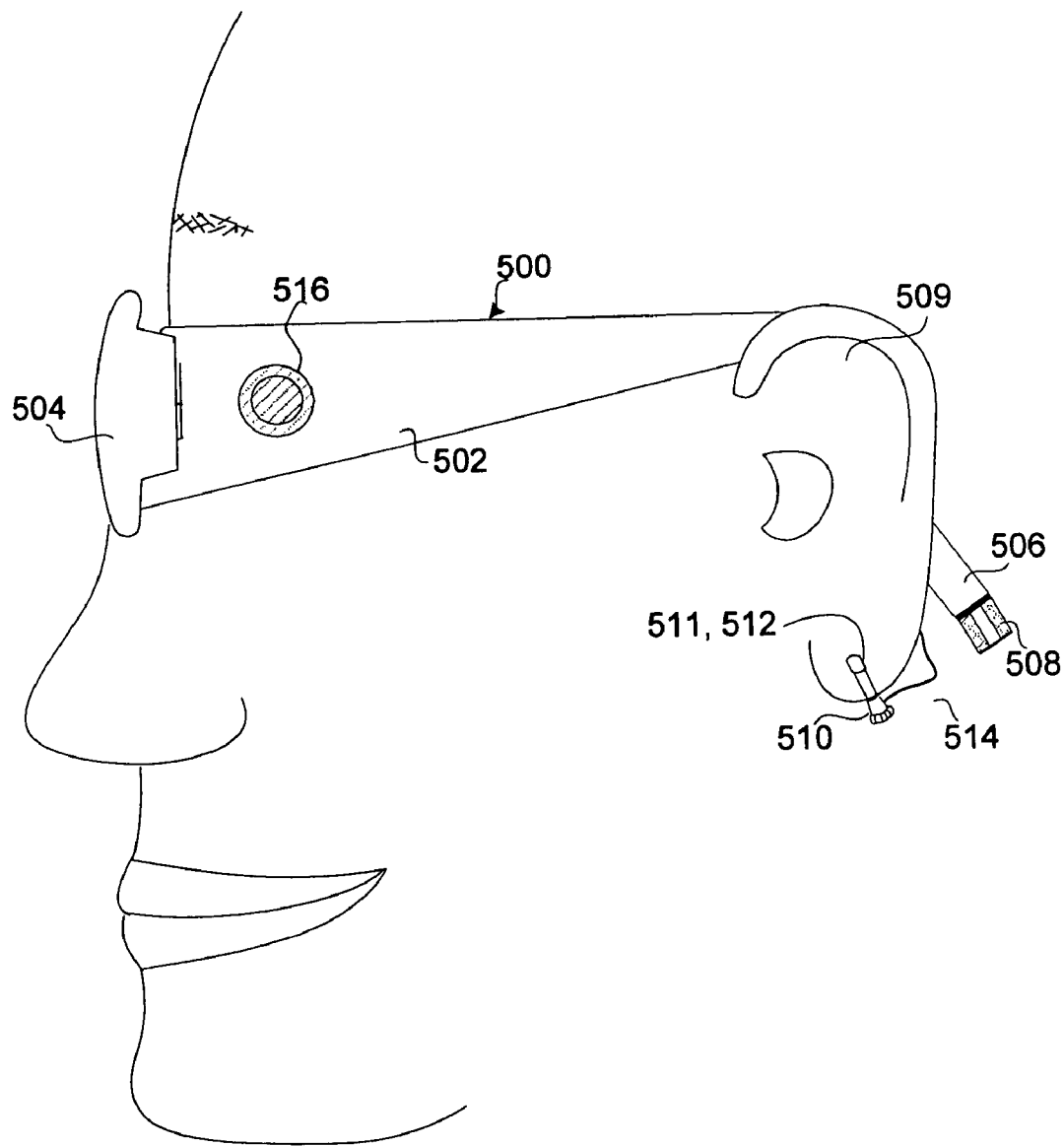
FIG. 1 shows a person wearing a pair of glasses with a heart rate sensor according to an embodiment of the invention.

FIG. 1 illustrates a pair of eyeglasses 500 having heart rate monitoring capabilities according to one embodiment. The pair of eyeglasses 500 includes left and right temples 502 and left and right lens holders 504.

A rearward temple portion 506 (e.g., temple tip region) of at least one of the temples 502 includes an electrical connector 508. As an example, the electrical connector 508 is a standard connector such as a 3.5 mm mini-phone connector or a bus connector (e.g., USB connector). In FIG. 1, the connector is depicted to be at the end of a temple. The connector or a different connector could be at other locations as described in related applications, which have been incorporated by reference. The electrical connector 508 enables the eyeglasses 500 to easily connect with other electrical devices, such as a computing device.

In addition, the eyeglasses can be coupled to a clip 510 having an infrared (IR) transmitter 511 and an IR receiver 512 on opposite sides of one end of the clip 510. In one embodiment, an IR sensor includes the IR transmitter 511 and the IR receiver 512.

In operation, the clip 510 is clipped to a body part of the user, such as one of the user's ears. Different parts of the ears could be clipped, such as the ear lobe (as illustrated in FIG. 1) or the upper portion 509 of the person's ear. During measurement, at least a portion of the IR radiation from the transmitter 511 transmits through the body part that is clipped, and is received by the IR receiver 512 to be measured. For example, when an ear lobe is clipped as depicted in FIG. 1, the ear lobe is sandwiched between the IR transmitter 511 and the IR receiver 512.

The IR sensor is electrically connected to processing circuitry. In one embodiment, the processing circuitry can be at least partially embedded in the eyeglasses (e.g., in at least one of the temples), and is electrically connected to the IR sensor through a cable 514. Alternatively, the cable 514 could have an electrical connector at one end that can removably couple to the electrical connector 508 at the glasses. This would allow the IR sensor to be detachable from the glasses, and to be electrically connected with the processing circuitry via electrical connectors when needed.

In one implementation, the clip 510 is a small spring-clip, the IR transmitter 511 is an IR LED, and the IR receiver 512 is a silicon photodiode.

In another embodiment, the IR sensor further includes a red light source (e.g. a red LED) and a light receiver (e.g. a light photodiode). In this embodiment, the heart rate sensor monitors heart rate by a combination of IR and red light.

Figure 2:
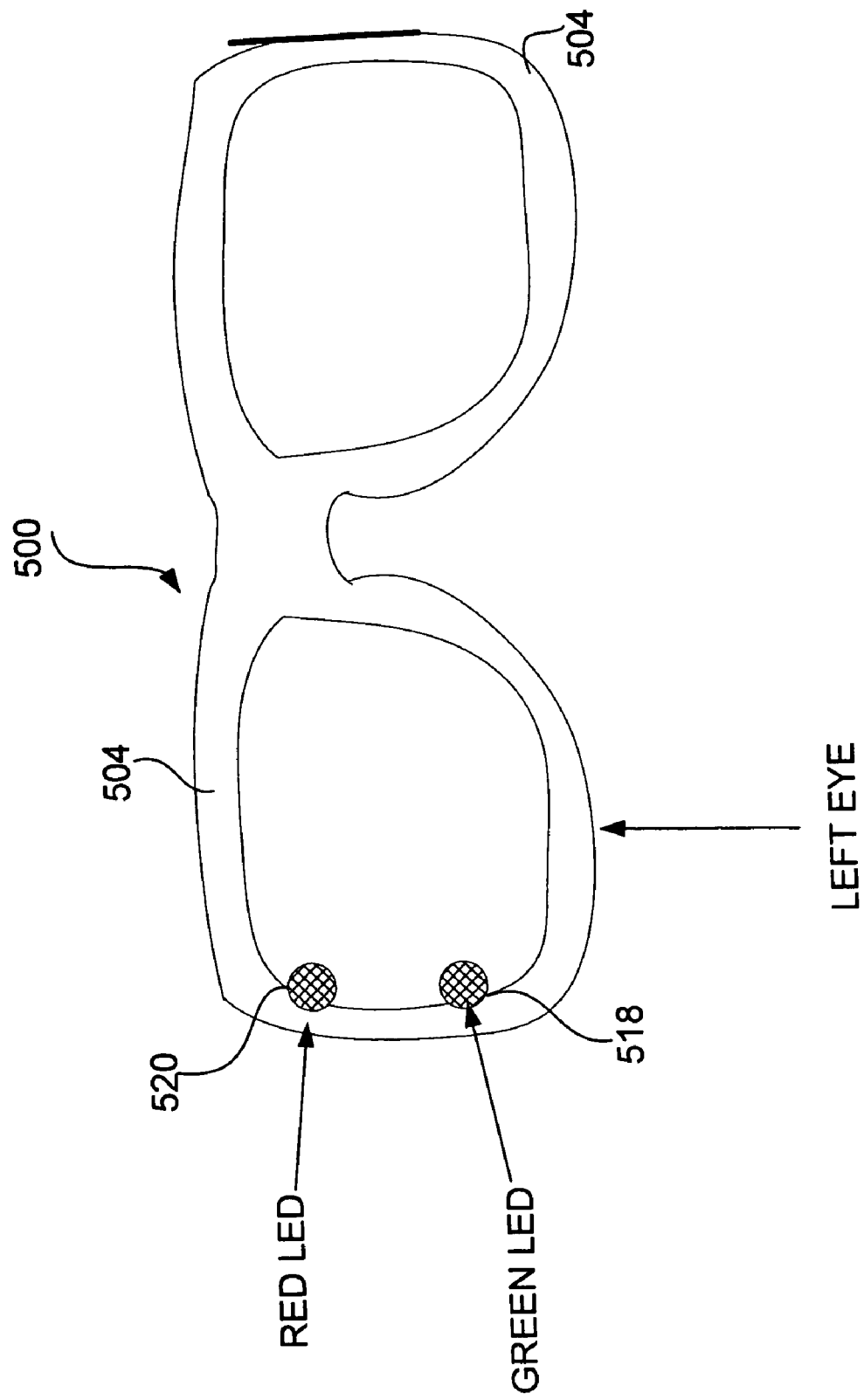
FIG. 2 shows a pair of glasses with LED as outputs according to an embodiment of the invention.

The eyeglasses 500 can also include at least one switch 516 and one or more output devices, which could be visual indicators. The switch 516 can serve as a start switch. In one embodiment, visual indicators, as shown in FIG. 2, can be located on the interior of a lens holder, such as the left lens holder 504. In another embodiment, visual indicators are located at relatively inconspicuous locations that could be seen by the user without taking the glasses off. For example, the visual indicators can be located on the interior of a temple, close to its end that connects with the corresponding lens holder. In one embodiment, the visual indicators are LEDs. For example, the eyeglasses 500 include a first LED 518 (e.g., green LED) and a second LED 520 (e.g., red LED).

FIGS. 3A-3D shows examples of circuits to measure the pulse of a user according to an embodiment. The examples serve as illustrations, and other types of circuits could be used. In general, the circuits include an infrared LED and a photodiode. The LED and the photodiode could be on opposite sides of a clip, which is clipped onto a part of the user, such as her ear lobe during measurement. The output of the photodiode is a function of the amount of flesh or tissue between the photodiode and the LED. If the distance between the photodiode and the LED changes, the output could change. The output is also a function of the blood pulsing through the tissues. The amount of output due to the tissue could be manifested as a DC offset, which is combined with the pulsing signals due to the blood going through the tissue.

In one embodiment, the circuits measure the pulse of the user by stabilizing the outputs from the IR sensor (such as with a feedback loop), filtering out the DC offset and amplifying the outputs to extract the pulse signals.

Figure 3A:
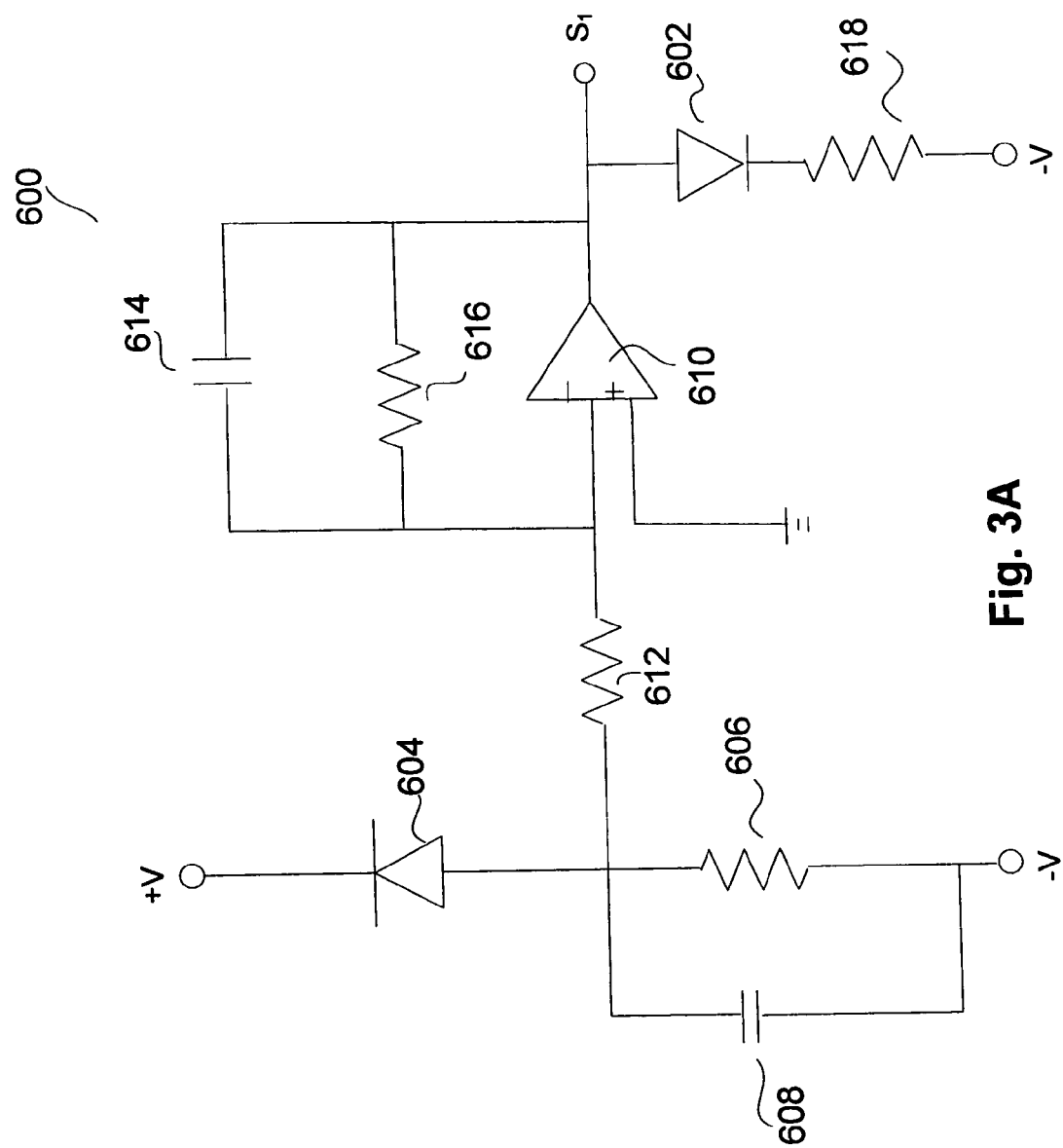
FIGS. 3A-D show examples of circuits to measure the heart rate of a user according to different embodiments of the invention.

FIG. 3A illustrates an example of an input circuit 600. The input circuit 600 uses a feedback loop to stabilize the outputs from an infrared LED 602, which radiates infrared to be received by a photodiode 604. The negative terminal of the photodiode 604 is connected to a voltage source V, such as 4.5 volts. The positive terminal of the photodiode 604 is connected to a low-pass filter with a resistor 606, such as 100 KΩ, and a capacitor 608, such as 0.22 µf, in parallel. The low pass filter has a cut-off frequency of 7 Hz. The other end of the low-pass filter is connected to a voltage source −V, such as −4.5 volts. The cathode terminal of the photodiode is connected through a resistor 612, such as 1 MΩ, to the negative input of an operational amplifier ("opamp") 610, such as a LM324. The positive input of the opamp 610 is connected to ground. The negative input of the opamp 610 is also connected to its output through another low pass filter, with a cutoff frequency of 3.4 Hz. This low pass filter has a resistor 616, such as 10 MΩ in parallel with a capacitor 614, such as 0.005 µf. The output of the opamp 610 is connected to the positive terminal of the infrared LED 602, whose negative terminal is connected to ground through a resistor 618, such as 180Ω. The output of the opamp 610 is designated as S1. In one embodiment, the opamp 610 changes or modulates the output from the LED 602 so as to keep the signals from the photodiode 604 to be about the center of its operating range. In one example, the signals S1 are about 0.2 volts±0.01 volt. The pulse signals substantially vary between the ±0.01 volt.

Figure 3B:
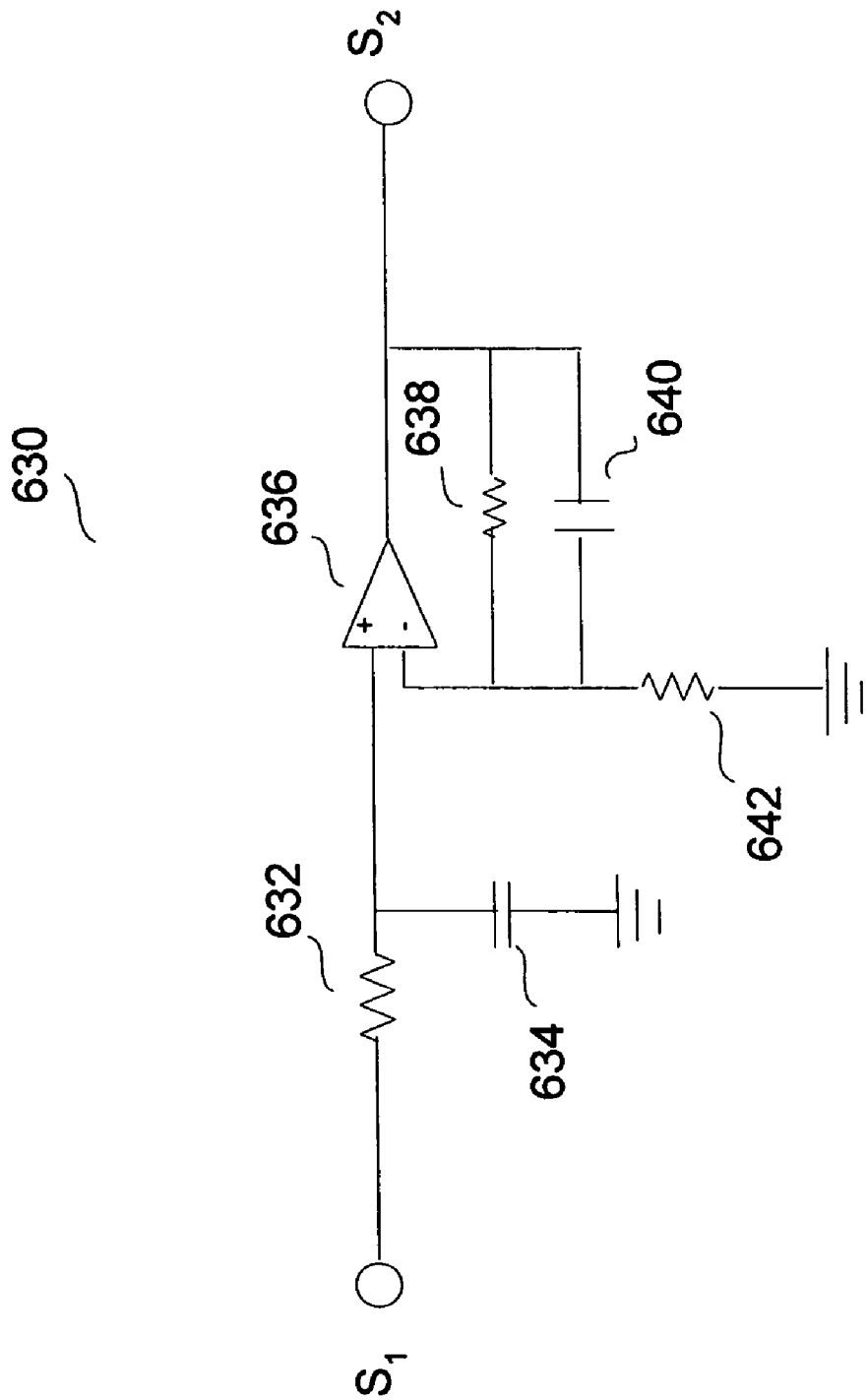

FIG. 3B illustrates an example of a two-pole low pass filter 630. Through a first low pass filter with a cutoff frequency of 16 Hz, the signals S1 are received by the positive input of an opamp 636, such as a LM324. The low pass filter has a resistor 632, such as 1 MΩ, connected to a capacitor 634, such as 0.01 µf, and then to ground. The junction of the resistor 632 and the capacitor 634 is connected to the positive input of the opamp 636. The negative input and the feedback loop of the opamp 636 have another low pass filter, also with a cut off frequency of 16 Hz. This low pass filter includes two resistors and a capacitor. One resistor 642, such as 1 MΩ, is connected from the negative input of the opamp 636 to ground. Another resistor 638, such as 1 MΩ, in parallel with the capacitor 640, such as 0.01 µf, is connected between the negative input and the output of the opamp 636. The signals at the output of the opamp 636 are designated as S2.

Figure 3D:
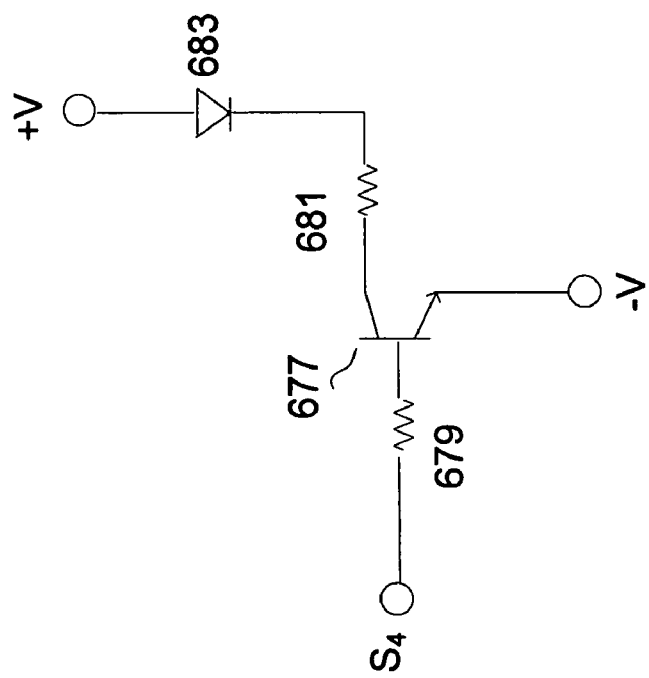
Figure 3C:
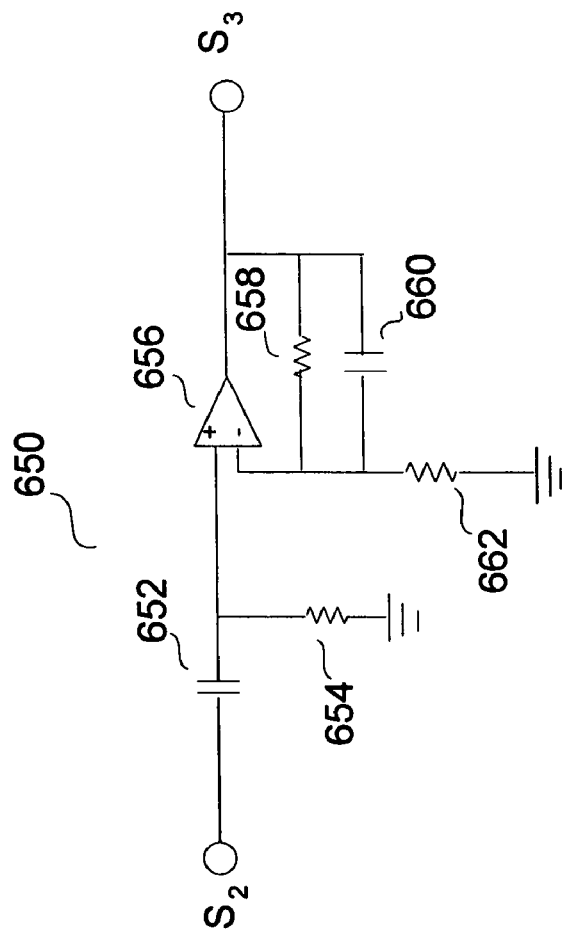

FIG. 3C illustrates an example of a bandpass filter 650, which at least serves to remove constant or DC signals from the pulse signals. Through a high pass filter with a cutoff frequency of 0.36 Hz, the signals S2 are received by the positive input of an opamp 656, such as a LM324. The high pass filter has a capacitor 652, such as 0.22 µf, connected to a resistor 654, such as 2 MΩ, and then to ground. The junction of the capacitor 652 and the resistor 654 is connected to the positive input of the opamp 656. The negative input and the feedback loop of the opamp 656 have a low pass filter, with a cut off frequency of 16 Hz. This low pass filter includes two resistors and a capacitor. One resistor 662, such as 10 KΩ, is connected from the negative input of the opamp 656 to ground. Another resistor 658, such as 1 MΩ, in parallel with the capacitor 660, such as 0.01 µf, is connected between the negative input and the output of the opamp 656. The signals at the output of the opamp 656 are designated as S3.

The signals S3 are received by another bandpass filter, similar to the one depicted in FIG. 3C, to produce signals S4. Through a high pass filter with a cutoff frequency of 0.36 Hz, the signals S3 are received by the positive input of another opamp, such as a LM324. The high pass filter has a capacitor, such as 0.22 µf, connected to a resistor, such as 2 MΩ, and then to ground. The junction of the capacitor and the resistor is connected to the positive input of the another opamp. The negative input and the feedback loop of the another opamp have a low pass filter, with a cut off frequency of 16 Hz. This low pass filter includes two resistors and a capacitor. One resistor, such as 3.3 KΩ, is connected from the negative input of the another opamp to ground. Another resistor, such as 1 MΩ, in parallel with the capacitor, such as 0.01 µf, is connected between the negative input and the output of the another opamp. The signals at the output of the another opamp are the signals designated as S4.

The signals S4 are then received by the base of a transistor 677 through a resistor 679, such as 100 KΩ, as shown in FIG. 3D. The collector of the transistor 677 is connected to a resistor 681, such as 1 KΩ, which is then connected to a LED 683, and then to +V. The emitter of the transistor 677 is connected to −V. In this example, the LED 683, such as a red LED, blinks at the rate of the pulse; the LED 683 serves as an output indicator. Instead of a LED output, in an alternative embodiment, the glasses can use audio instead of or in addition to visual clues. In such cases, the glasses may support a speaker or other types of output mechanisms, such as LCD, as discussed in this or related patent applications incorporated by reference.

In another embodiment, the signals S1 could be sent to the input of an analog-to-digital converter, whose outputs are received by a digital signal processor to digitally process the signals.

Typically, when worn, a pair of glasses is in a stable position relative to the user's head and ears. The stability serves as a good platform for a heart rate sensor. Though the glasses serve as a stable platform, there can still be noise. With the clip applied to the user, if the user moves, the wire 514 could move with her, which, in turn, could move the clip 510 relative to the user. The heart rate signals from the sensor could be small relative to, for example, noise signals or the DC offset. As an illustration, a clip that moves during measurement could change the DC offset because the amount of tissue compressed or measured by the clip could change. This change in DC offset could produce noise, reducing the signal-to-noise ratio.

There are different techniques to enhance clip stability when clipped to the user. One can increase the pressure of the clip. However, the pressure from the clip should not be too strong because this could be uncomfortable to the user.

Figure 4:
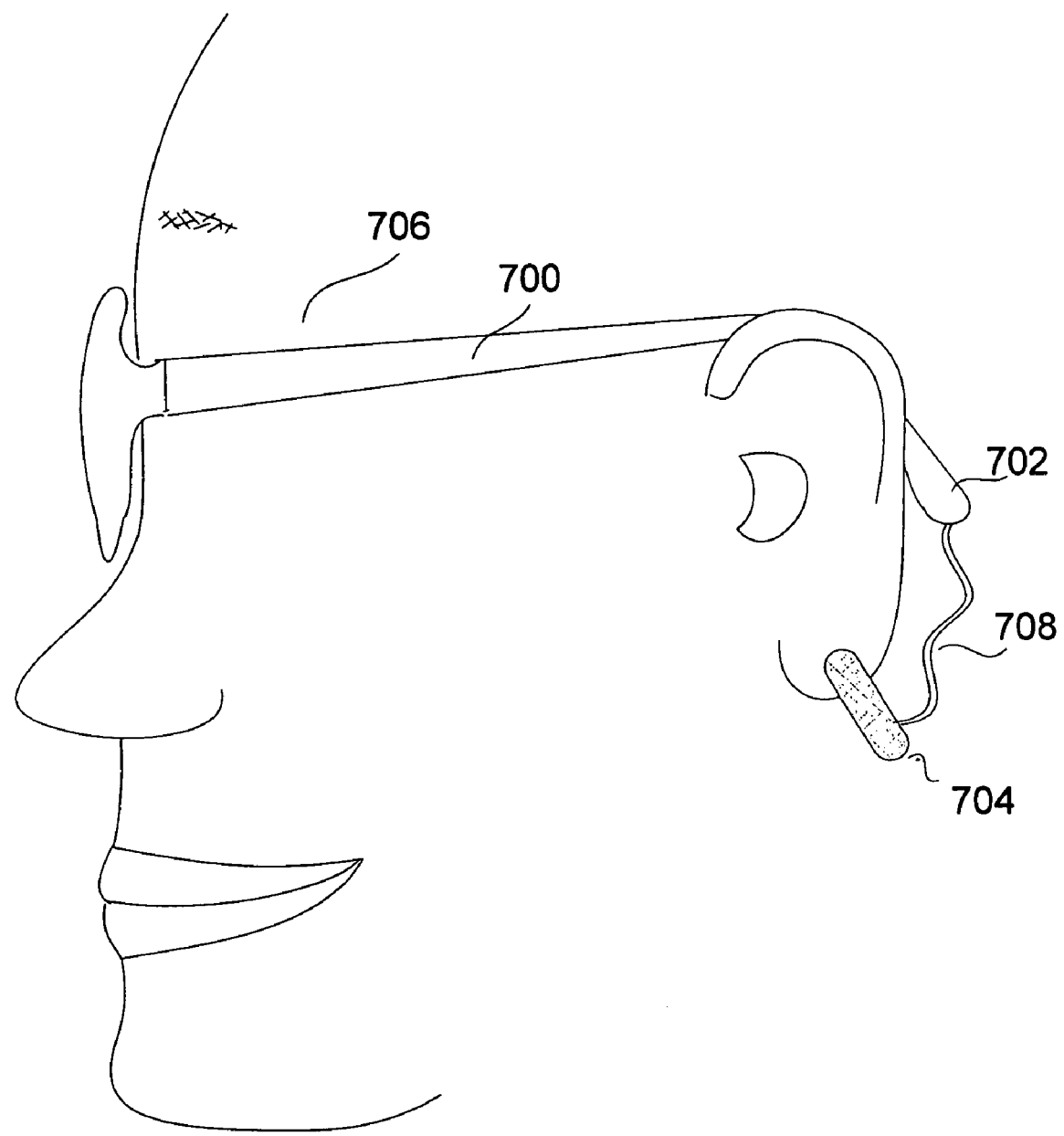
FIG. 4 shows a heart rate sensor clip being attached to the tip of a temple of a pair of glasses according to an embodiment of the invention.

Another approach to enhance clip stability is to reduce the length of the wire 514. FIG. 4 shows a sensor clip 704 being attached to the tip 702 of a temple 700 of a pair of glasses 706. If the wire moves, a shorter wire 708 would reduce its pulling on the clip because the wire has a smaller inertia.

In one embodiment, at least a portion of the heart rate processing circuitry is in a portable device (not in the glasses). The portable device is carried by the user, and a wire attaches the portable device to a heart rate sensor in a clip. The wire 514 at the glasses is typically shorter than the wire from the portable device carried on most other parts of the user because the glasses are just adjacent to the clip. A shorter wire makes its pulling force on the clip smaller. As a side note, in the example shown in FIG. 4, the wire 708 is directly attached to the temple tip region 702 of the glasses, without requiring a connector. In another embodiment, there could be an electrical connector at the end of the wire 708, and the connector could attach to a connector at the glasses.

In one embodiment, given that a heart rate sensor is attached to or held against the user's head, the wire connecting the sensor to a pair of glasses worn by the user is relatively short in length. For example, the length of the wire (which could include a number of insulated conductors) in one embodiment, can be not more than eight (8) inches; in another embodiment, not more than six (6) inches; in another embodiment, not more than four (4) inches; in another embodiment, not more than three (3) inches; in another embodiment, not more than two (2) inches; and in another embodiment, not more than one (1) inch. The relatively short wire can reduce potential sources of noise and can render the corresponding heart rate monitor/sensor more comfortable for the user.

Figure 5:
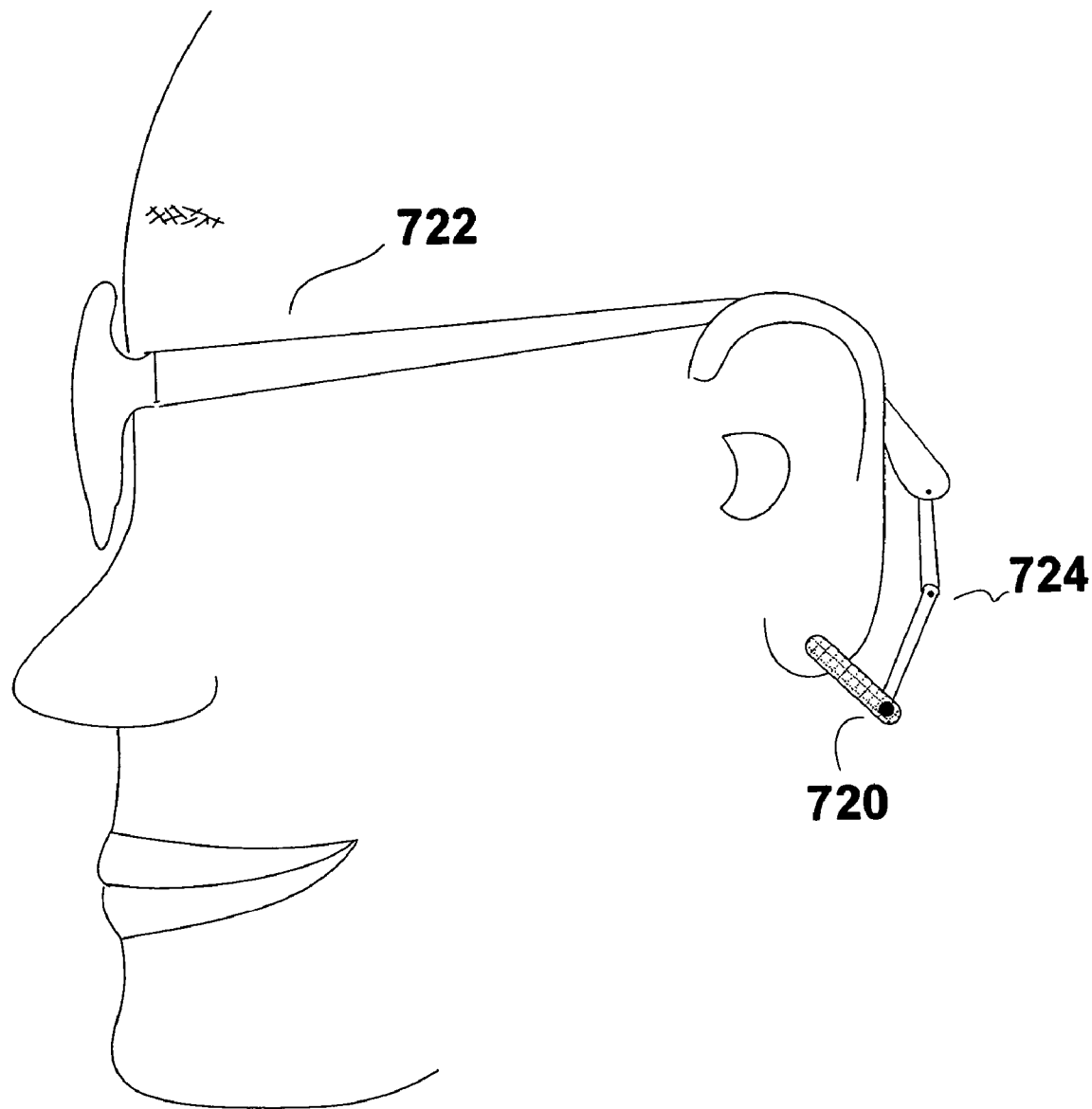
FIG. 5 shows a heart rate sensor clip being attached through an adjustable mechanical arm to a temple of a pair of glasses according to an embodiment of the invention.

Another approach to enhance clip stability is to couple the clip to the glasses by a more rigid element. In other words, if the heart-rate monitor is more rigidly or substantially rigidly attached to the user during measurement, the measured results can also be more stable. Since the glasses are quite stable when worn, if the clip is more rigidly tied to the glasses, the clip is also relatively stable. In one approach, instead of a thin wire, an adjustable mechanical arm that is more rigid than a thin wire is used to connect the clip to the glasses. Though more rigid, the arm is adjustable to accommodate for people with different size ears and/or heads. FIG. 5 shows an example of such an embodiment. In this example, the sensor clip 720 is connected to the glasses 722 through an adjustable mechanical arm with two sections linked by a hinge. The hinge could be made relatively stiff to reduce the motion of the arm relative to the clip 720. The heart rate sensor in the clip 720 could be electrically connected to electronics in the glasses through one or more conducting wires embedded inside the arm 724.

Figure 6:
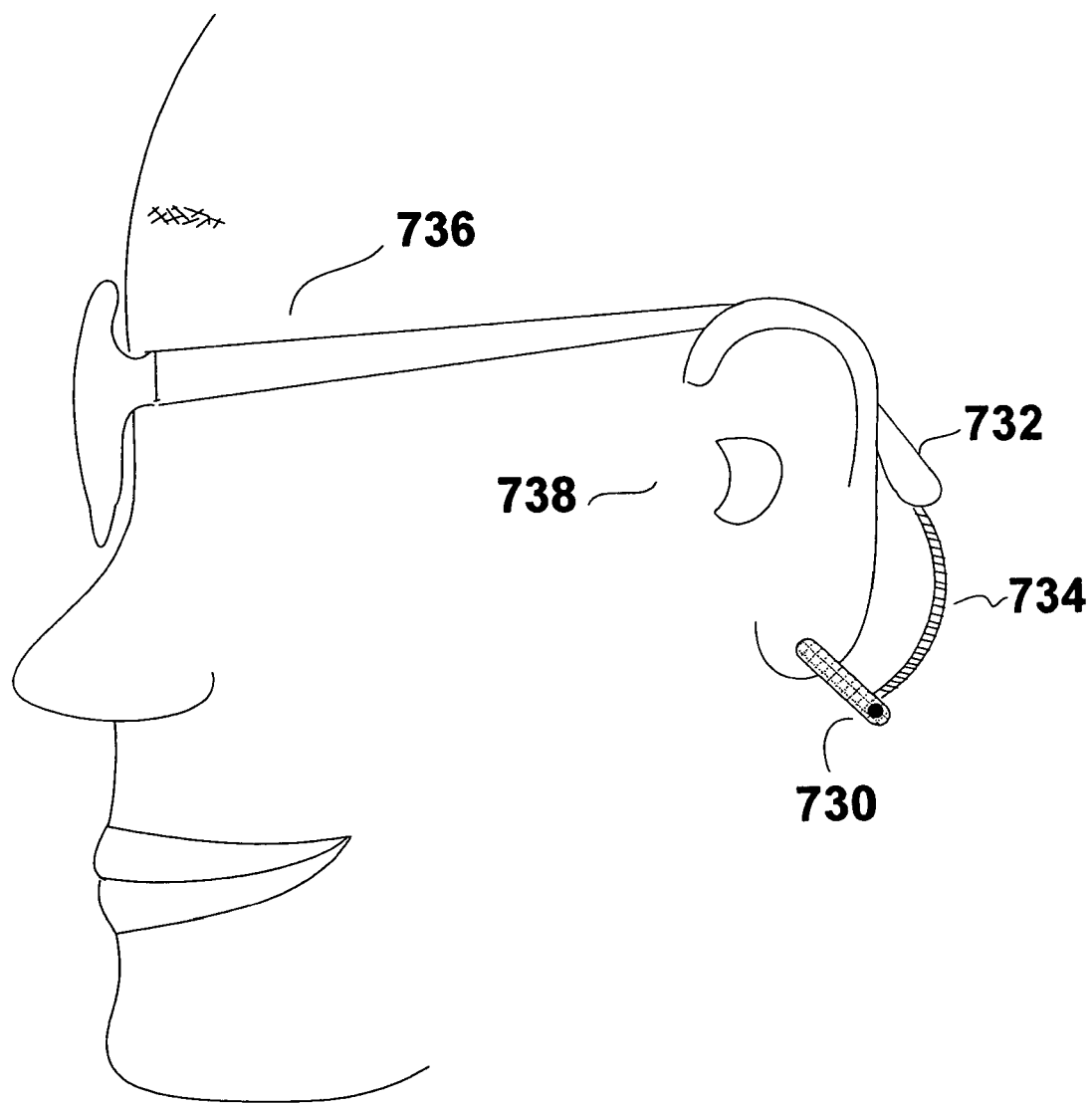
FIG. 6 shows a heart rate sensor clip being attached through a semi-rigid arm or cable to a temple of a pair of glasses according to an embodiment of the invention.

In another embodiment, the clip can be more rigidly or substantially rigidly attached to the user during measurement by a stiff wire 514, such as by making the wire with a thicker cable. This can reduce movement of, or substantially immobilize the clip. FIG. 6 shows an example of a clip 730 being attached through a semi-rigid cable 734 to a temple tip 732 of a pair of glasses 736. The cable is semi-rigid, and is malleable enough to allow the location of the clip 730 to be adjusted relative to an ear 738. In one embodiment, the cable could be a number of insulated solid copper wires, in the range of 18 to 26 gauge, bundled together. In another embodiment, the cable could be a number of insulated conductor wires, each being, for example, 22 AWG solid copper wire. The heart rate sensor in the clip 730 could be electrically connected to electronics in the glasses through insulated copper wires bundled to form the cable 734.

A number of techniques have been described on stabling the wire or the clip relative to the glasses. In one embodiment, the glasses could also be stabilized by a strap. One example of a strap is a sport strap that snugly attaches or secures the glasses to the user's head. Such a strap is typically used for sport activities. The two ends of the strap could be coupled to the temples of the glasses, and can be located close to their corresponding lens holders. The coupling can be based on mechanical connectors (e.g. snaps, clips), part of which may be integral with the temples of the glasses, and the other part integral with the straps. In another embodiment, the strap could be a lanyard.

One reason to reduce the mobility of the wire 514, the clip 510 and/or the glasses is that this may increase the stability of the signals from the heart rate sensor, or to increase the signal-to-noise ratio. In one embodiment, the signal-to-noise ratio could be enhanced through signal processing techniques, such as digital signal processing techniques. For example, a digital signal processor could average the IR sensor outputs, such as the signals S1 of the embodiment shown in FIG. 3A. In another embodiment, an output signal from the sensor is ignored if the signal differs from its immediate prior signal measured at a predetermined interval earlier, by more than a preset %. The rationale is that a person's heart rate cannot change too drastically. If the output changes beyond a certain predefined threshold from its prior value, the likelihood is high that the output is erroneous. In yet another embodiment, an output is accepted only if it is within a certain predetermined threshold of the average of a number of its prior readings. For example, the output is accepted if it is within 30% of three of its prior readings, which could be readings or sensor outputs taken at an interval of every 2 seconds.

A number of embodiments have been described where the processing circuits are in the glasses. In one embodiment, the IR sensor output (or the signal after some processing, such as amplification, of the sensor output), is transmitted through a cable connected from the connector 508 at the glasses to a portable device. The portable device could be carried by the user and the portable device could further process the received signals. In other words, some processing of the signals can be performed at another computing device connected to the glasses. Instead of through wired connection, in another embodiment, the electrical connection is performed wirelessly. In this wireless embodiment, the glasses include wireless circuits to transmit the sensor outputs (or after some processing of the sensor outputs or signals regarding the heart rate of the user of the glasses) to another computing device to be, for example, displayed. The another computing device could be a portable or handheld electronics device the user carries. Different wireless transceiving (transmitting and receiving) capabilities in the glasses have been described in related applications, which have been incorporated by reference.

Instead of wirelessly coupled to a portable or handheld device, in another embodiment, signals from electronics in glasses (or information regarding the user's heart rate) are wirelessly coupled to and used by an electronic stationary device. The device or machine is designed to be non-portable or non-handheld, such as a stationary bike, treadmill or stair stepper machine. In one embodiment, the operations of the stationary device are modified based on the received signals. For example, the device is a treadmill, which includes a number of workout programs. In one embodiment, a workout program in the treadmill depends on the measured heart rate of the user. For example, in a normal sequence, the program will increase the speed of the treadmill. However, in view of the tracked heart rate of the user, the program maintains the speed of the treadmill.

The eyeglasses as described in this application can be used to measure the user's heart rate on demand by the user, or passively or automatically once every predetermined amount of time. Also the user's heart rate can be measured over a duration of time, such as during an exercise routine or program.

A representative example of using the eyeglasses 500 during an exercise routine is explained as follows. The user can be skiing, biking or jogging; and the eyeglasses can be a pair of skiing goggles, an eyeglass frame designed for exercise, or a pair of sunglasses. Back to the exercise routine, first, the user puts on the glasses 500 and clips the clip 510 to her earlobe. Next, the start switch 516 is activated (e.g., pressed). Assume that the user is resting and does not have an elevated heart rate when the start switch 516 is activated. Next, green/red signals from green/red LEDs, 518 and 520, continue to blink till the sensor has finished measuring the user's resting heart rate. One way the sensor stops blinking is when the measured heart rate does not change more than a predefined threshold for a few measurements.

Note that instead of green/red blinking signals, there could be other type of output mechanisms pertaining to any of a variety of visual and/or audio indicators. For example, the visual output mechanism can be a LCD display or can be one or more LEDs. After a preset amount of time, such as 15 seconds, the initial measurement is complete, and only the green LED blinks, thereby indicating that the user can begin her workout. During the workout, the LEDs can have the following meanings:

Blinking red: too fast—slow down.
Blinking green: too slow—speed up.
Solid green: just perfect—maintain your pace.
Red/Green: the program is about to change to a new sequence.

In one embodiment, such as with blinking green signals, the user is further notified that her pace is too slow to burn calories, and she should speed up. The notification could be through different mechanisms, such as through audio signals or other visual signals, or both. After the workout is over, the display shows solid Red and solid Green for a preset amount of time, such as 15 seconds, and then goes off. If the user wants to extend the workout, the user could activate the switch 516 again (e.g., press the switch button once for about ½ second) and then the glasses will add another 10 minutes to the workout.

In one embodiment, the recommended pace of exercise depends on the age and sex of the user. For example, the user's age and sex are entered into the glasses. Based on such information, the glasses automatically determine the range of appropriate heart beats per minute for optimum exercise. Based on the heart rate measured, the glasses would recommend the user to go faster or slower so as to fall within the range.

In another embodiment, the glasses include a speaker, which instructs the user regarding a workout program. For example, the glasses could instruct the user to continue at the same pace of exercise (e.g. to maintain the same heart rate) for the next 5 minutes. At the end of the 5 minutes, the glasses would instruct the user to, for example, stop running, and start walking (e.g. to reduce the heart rate).

Hence, the heart rate monitoring provided with the glasses is convenient and useful for those desirous of an effective workout. The glasses can help the user maintain the user's heart rate within the proper window for optimum fitness, which could be entertaining to some people during their workout.

In another embodiment, the glasses can include a memory device so that one or more workout programs and/or songs can be stored. The memory device could be, for example, attached to or integral with the glasses. With workout programs as examples, a switch could be used to select a workout program. There are many different workout programs available. In one embodiment, workout programs can be downloaded from a website to the glasses (e.g., wirelessly or using the connector 508). By downloading a new program, the user can make the selection. In one embodiment, the glasses can be connected to a port of a computer via a connector (e.g., the connector 508) for downloading.

In one embodiment, the operations of a workout program depend on the measured heart rate of the user. As an example, before the user starts her workout, the heart rate of the user is measured and kept track of. Then, the user starts the workout program. The workout program could be for jogging. The program tracks the user's heart rate as a function of time. As the heart rate increases, the program could provide indication to the user as to whether the user should run faster (i.e. increase heart rate) or run slower or maintain speed.

In another embodiment, the glasses could play songs, which could be stored in a memory device inside the glasses or attached to the glasses, such as based on a digital audio format (e.g., MP3 format). For example, an exercise program would tell the user what to do, such as keep the same walking pace. Then for the next 5 minutes, the glasses play songs for the user. The user could select the songs to play based on one or more switches or control mechanisms on the glasses. Or there could be a display at or coupled to the glasses, and the display has a user-interface program to help the user select songs. Additional descriptions regarding providing audio entertainment through glasses are in related applications, which have been incorporated by reference.

In one embodiment, the speed of the song or entertainment depends on the measured heart rate. For example, if the exercise program wants the user to run faster, the program would instruct the user to run following the beat of the music, and the song is played at a faster pace. In another embodiment, the type of songs changes depending on the exercise routine. For example, a fast song would be played if the user should bike faster, and a slow song would be played if the user should bike slower. In one embodiment, the songs could be picked or categorized by the user. In other words, the user could select songs and categorize them accordingly, such as some under the category of "fast" and some under the category of "slow." Then when a fast song should be played, a fast song designated by the user would be selected.

In one embodiment, the user enters her weight into the glasses, or into a memory device coupled to the glasses. This again can be done by using, for example, one or more switches at the glasses (or the memory device) or downloaded to the glasses (or the memory device) through the connector 508, or downloaded wirelessly. Based on the weight and the monitored heart rate as a function of time, processing circuitry could more accurately estimate the calories burnt by the user as the user exercises, or after the user has exercised for a duration of time.

A number of embodiments have been described regarding pressing or activating a switch at the glasses. For example, the activation can be for turning on monitoring electronics in a pair of glasses. In one embodiment, turning on the monitoring electronics in the glasses is done remotely. The pair of glasses includes a wireless receiver that constantly listens to activation signals. When such a signal is received, the monitoring electronics in the glasses are automatically activated, such as activating a heart-rate sensor to start measuring heart-rates. With such an embodiment, a user does not have to physically interact with the glasses to turn on the monitoring electronics, or to enter information into the glasses.

In yet another embodiment, heart rate is measured to monitor a health problem or issue of the user. For example, the user constantly suffers from irregular heartbeat (or arrhythmia). There could be skipped heart beats, fluttering or 'flip-flops', or uncontrolled rapid heart beat. The heart's rhythm may be normal or abnormal, and treatment depends on the type and seriousness of the arrhythmia. Sometimes one does not need treatment. However, in other situations, one might need medication, to make lifestyle changes or to even go through surgery.

In one embodiment, the glasses keep track of the user's heart rate. If the heart rate is irregular (e.g. suddenly goes very fast, instead of gradually increasing), the glasses would provide an indication to the user to relax. The glasses could include a program to guide the user through a relaxation routine, such as a breathing exercise.

In another embodiment, the glasses keep a record of the user's heart rate, such as (a) when irregular heart beat occurs, (b) the duration of the irregular heart beat and the heart rate at the time of the irregular heart beat, (c) whether the irregular heart beat is slow or fast, and/or (d) whether the irregular heart beat begins or ends suddenly. Such recorded information can be stored in a memory within or attached to the glasses and can be downloaded to other devices, such as for a doctor to help treat the user. The downloaded heart beat information could be displayed visually in different formats, such as in a graphical format as a function of time.

In one embodiment, if the condition of the irregular heart beat is beyond a predetermined threshold, the user will be alerted to call for medical help. For example, predetermined thresholds could be based on the number of extra heartbeats per minutes, the number of runs of such irregular heart beat within a predetermined duration of time, and/or the heart beat being more than a certain number per minute without exercise or fever.

In another embodiment, the electronics in the glasses include wireless communication (e.g., cellular phone) capabilities. Such capabilities have been described in related applications, which are incorporated into this application by reference. If the irregular heart beat condition is beyond one or more of the predetermined thresholds, the phone or wireless transmitter would automatically initiate a call or transmits a wireless signal to a medical facility to ask for help for the user. Or, the call (or signal) could be sent to a previously defined designated number or location, which could be to a relative of the user. In another embodiment, short-range wireless communication is established with a portable device carried by the user. The portable device then initiates the call.

Yet another embodiment includes a temple arrangement, such as a temple tip, that is detachable from the glasses, and can be acquired after the purchase of the glasses. There is at least one electrical component in the temple arrangement. The electrical component in the temple arrangement could interact with another electrical component in the frame of the glasses, or in a device tethered or coupled to the glasses. For example, a temple of a pair of glasses holds one portion of an electrical circuit. That portion can include generic parts, such as a battery, that are applicable to different applications. The battery can be rechargeable. In one embodiment, a pair of glasses includes a connector to allow a rechargeable battery inside the glasses to be charged. Another portion of the electrical circuit includes more application-specific parts, and that portion is in a temple arrangement. As an example, this application-specific portion can be for monitoring heart rate. The temple arrangement can be an after-market product that a user can separately acquire after getting a pair of glasses. In another embodiment, all the electronics, both the generic parts and the application-specific parts, are in a temple arrangement. In yet another embodiment, all the electronics are in a temple or a portion of a temple, which could be acquired after market. Different embodiments regarding temple arrangements have been described in related applications, which are incorporated into this application.

As described above, one way to stabilize a pair of glasses to a user's head is to use a strap or a lanyard to hold the glasses to the user's head. In one embodiment, the IR sensor is not at the glasses, but is attached to, integral with or tethered to the strap or lanyard based on different techniques as described above, or in related applications incorporated by reference.

In yet another embodiment, a pair of glasses as described in this application is replaced by an apparatus that is designed to be worn by the user in the vicinity of the user's head. Examples of an apparatus include a headband or a hat. In one embodiment, the hat can be a helmet. A headband or a hat can include cloth, and the heart-rate monitor can be attached to the cloth. Different embodiments on attaching electronics to garments or cloth have been described in related applications and are incorporated into the present application by reference.

In one embodiment, the apparatus designed to be worn by the user is a swimming cap. For example, the swimming cap conforms to the head of the user, and can cover the ears of the user. An IR sensor could be in a clip, such as one of the clips described in this application. The clip could be in the vicinity of an ear lobe of the user, and the clip could be tethered to the inside of the cap. Electronics in the clip can be electrically connected to electronics in the cap. In operation, the user wears the cap, and the clip is clipped to the corresponding ear lobe to measure the heart beat of the user. Even when the user is moving rigorously, with the clip inside the cap and bound by the cap, such embodiments could be used to measure the heart beat of the user.

In one embodiment, electronics are also sealed or waterproofed. This would further enable the wearable apparatus to be used under water.

A number of embodiments have been described where an IR sensor is configured into a clip where infrared signals are transmitted through a human body part, such as an ear lobe, and then measured. In yet another embodiment, instead of measuring (or just measuring) the transmitted signals, a radiation sensor, such as an IR sensor, measures reflected signals. During operation, such a sensor can be structurally configured to substantially maintain a constant distance to the skin or body location the sensor is measuring.

Figure 7:
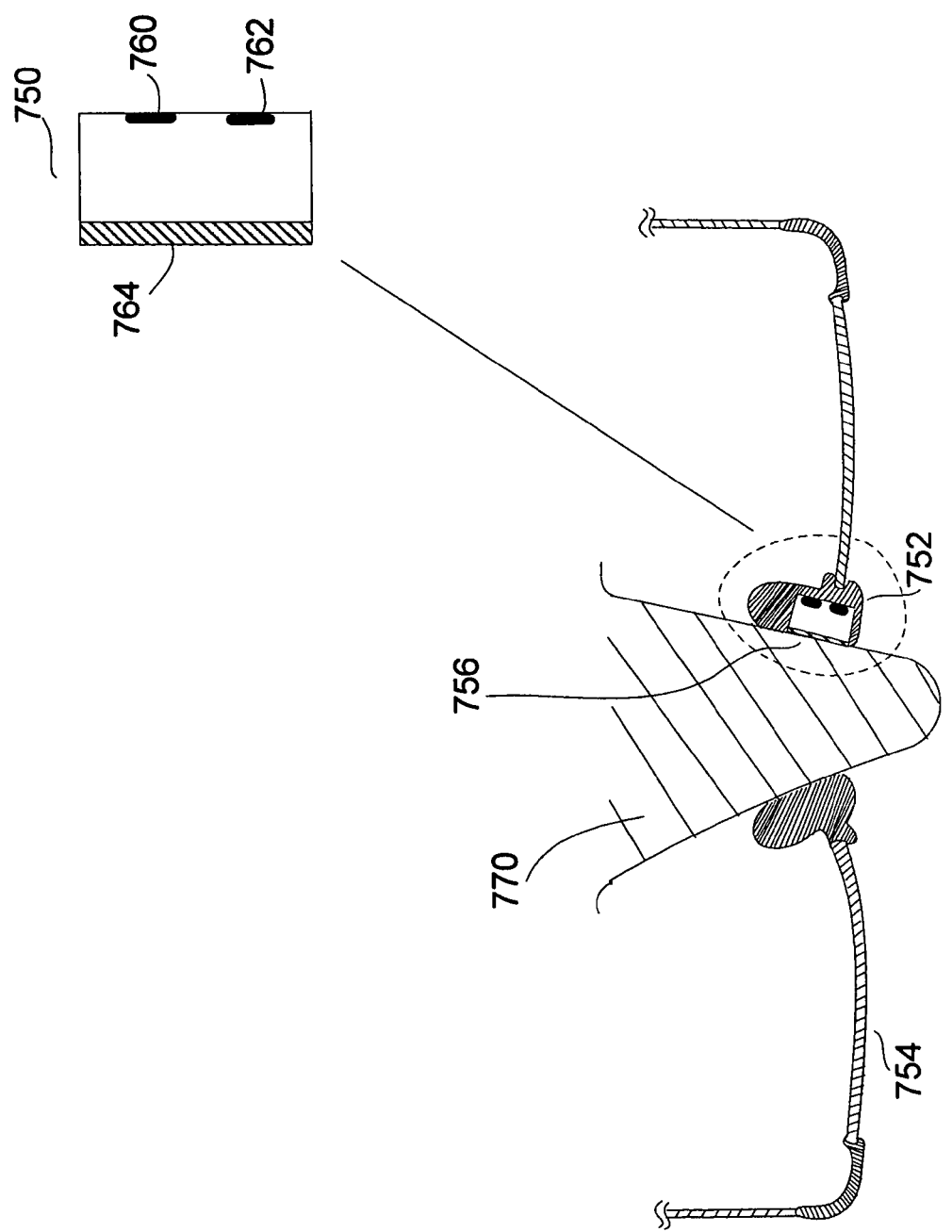
FIG. 7 shows a heart rate sensor that is based on measuring reflected signals according to an embodiment of the invention.

FIG. 7 shows one embodiment of a heart-rate sensor 750 based on measuring reflected signals. The sensor 750 could be at least partially embedded in a nose pad 752 of a pair of glasses 754 to measure the heart rate of the user. With the sensor 750 located at the nose pad 752, typically the distance between the sensor 750 and the position of measurement 756 is substantially maintained as a function of time and/or use when the glasses are worn. Also, with the sensor 750 at the nose pad 752, the sensor can be substantially or more rigidly attached to the user during measurement.

In one embodiment, the sensor 750 includes an IR emitter or transmitter 760, and an IR receiver or detector 762. In operation, IR radiation is emitted from the emitter 760 through a window 764 (such as an infrared window) and then is reflected at the position of measurement 756 of the nose 770. The reflected signals are detected by the IR detector 762. Based on such an embodiment, typically the distance between the sensor and the location of measurement on the nose are substantially constant or stable even when the user is performing relatively rigorous exercise. This could help to improve signal-to-noise ratio.

In one embodiment, one or more outputs from the sensor 750 can be processed by electronic circuits located at different parts of the glasses. For example, the sensor 750 can be in one nose pad, and the electronic circuits for outputs from the sensor 750 can be in the other nose pad. The circuits can be connected or coupled to the sensor 750 via conducting wires/cables in the bridge of the glasses. In another example, the circuits are in other parts of the frame of the glasses, such as inside a lens holder, in a hinge region between a lens holder and the corresponding hinge of the lens holder, or in a temple of the glasses. In yet another example, the circuits can be in a shield of the glasses, such as a shield that extends from a portion of a lens holder towards the face of the wearer of the glasses. These circuits can be coupled to the sensor 750 via conducting wires/cables embedded in the glasses. For example, the sensor 750 can be coupled to circuits in a hinge region via conducting wires embedded inside a lens holder, such as inside one of the lens holders of the glasses. In yet another embodiment, the coupling between the circuits and the sensor can be achieved wirelessly, and there can be a power source, such as a battery, in one of the nose pads.

Different types of electronic circuits are applicable to process the one or more outputs from the sensor 750. For example, circuits similar to those shown in FIGS. 3A-D can be used. In another embodiment, signals can be digitized and then digitally processed via a controller.

In yet another embodiment, the glasses are a pair of goggles. Electronics or processing circuitry at the strap, lens holder(s), the bridge and/or other part of the goggles interact with a heart rate sensor. In one approach, the heart rate sensor is based on measuring reflected signals, and is at a nose pad of the goggles. When worn, the goggles could be tightly fitted to the user, even when the user is moving rigorously. The sensor could interact with electronics in the goggles, as in different examples described in this application. In another approach, the goggles have soft rubber pads, and the heart rate sensor could be mounted or embedded in the goggles' soft rubber pad at a location that presses against the user's face when worn. In one embodiment, the sensor is configured to be embedded in the goggle's soft rubber pad in a fashion similar to the sensor embedded to a nose pad of the glasses shown in FIG. 7.

A number of embodiments have been described about a pair of glasses and/or other wearable apparatus having a heart rate monitor and/or a heart rate sensor. In yet another embodiment, the glasses and/or other wearable apparatus further includes one or more additional electronic devices, such as an activity sensor. One example of an activity sensor is a pedometer. Another example of an activity sensor is a positioning sensing device, which can be based on a global positioning system (GPS).

A pair of glasses for heart rate monitoring with functionality of a pedometer has a number of advantages. For example, the user has the health problem of irregular heart beat. It might not be accurate to determine whether the user has been exercising just based on her heart beat. However, the pedometer should be able to better indicate the amount of exercise the user has gone through. Another application is that if the user constantly experiences irregular heart beat, the pedometer would be able to better indicate the physical conditions of the user at the onset of the irregular heart beat, such as whether the user has been at rest or in motion.

Yet another application of a pair of glasses for heart rate monitoring with functionalities of a pedometer is on the condition of the irregular heart beat triggering a call for medical help. If the call is based on the heart rate exceeding a certain number per minute, that certain number can be a function of how rigorous the user has been exercising. In other words, the base line for triggering the call could depend on the output of the pedometer. Thus, if the heart beat sensor measures an elevated heartbeat, and the pedometer indicates that the user is exercising, a call may not be triggered. However, without exercise, the same elevated heartbeat could be considered a dangerous situation, and a call would be initiated.

Also, this predetermined elevated heartbeat can be personalized to the user because different user might have a different threshold. In one embodiment, this elevated heartbeat can be user-defined and/or entered by the user into the glasses.

A controller, such as a microcontroller in the glasses, could analyze signals from the heart rate sensor and the pedometer together, and initiate certain actions for the benefit of the user.

In another example, calories burnt by the user could be more accurately determined based on outputs from a heart rate monitor and a pedometer.

In one embodiment, a heart-rate sensor is at a nose pad and a pedometer is at a hinge region between a hinge and its corresponding lens holder of the glasses. Additional descriptions on pedometer in glasses could be found in related applications, which have been incorporated by reference.

Another example of an additional electronic device is a temperature sensor. The temperature sensor could keep track of the user's temperature. In one embodiment, a temperature sensor can be in a nose pad, and a heart-rate sensor can be in the other nose pad of a pair of glasses. As an example of an application, the user is running a marathon. It would be advantageous to monitor both the user's heart rate and temperature. In another embodiment, electronics in a pair of glasses can include a heart-rate sensor, a temperature sensor, a transceiver and a speaker. In addition to capturing information regarding the user's heart rate and temperature, the glasses can play music to the user.

In another embodiment, a pair of glasses does not have a heart-rate sensor. However, one of the nose pads has a temperature sensor. Additional descriptions on temperature sensors in glasses could be found in related applications, which have been incorporated by reference.

A number of embodiments have been described where the heart-rate monitor includes a sensor with a radiation transmitter and a radiation receiver to measure the heart rate. In one embodiment, the sensor includes a pressure sensor, such as a piezo-electric sensor. To measure heart rate, the sensor touches a part of the skin that has an artery below it. As the heart pumps blood flows through the artery, the artery expands and contracts. The sensor can sense the pulsation based on the change in pressure exerted on the sensor. For example, the sensor is positioned on top of the carotid artery. As another example, the sensor presses onto the temple region of a user's head. In one embodiment, the sensor is at an extension from an arm of a pair of glasses. The extension is close to a temple of the user. The position of the arm where the sensor is can press onto the temple of the user for heart-rate measurement. In another example, the sensor can be incorporated in an elastic band that can be wrapped around the user's neck, with the sensor positioned over the carotid artery of the user.

A number of embodiments have been described regarding a temple arrangement, such as a temple tip, that can be acquired after the purchase of the glasses. In one embodiment, different nose pads with different electrical components also can be acquired after market, or after the purchase of the glasses. These nose pads can replace the existing nose pads of a pair of glasses.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

A number of embodiments in the invention can be implemented in software, hardware or a combination of hardware and software. A number of embodiments of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Also, in this specification, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A pair of glasses for a user comprising:
   a frame for the glasses;
   a heart-rate monitor with at least a portion of the electronics of the heart-rate monitor being embedded in the frame, wherein the heart-rate monitor is configured to acquire heart rate data pertaining to the heart rate of the user;
   an electronic device at least partially embedded in the frame and configured to acquire user exercise data; and
   an audio output system configured to output audio signals containing heart rate information and/or exercise information, the heart rate information being dependent on the acquired heart rate data, and the exercise information being dependent on the acquired user exercise data.

2. A pair of glasses as recited in claim 1,
   wherein the heart-rate monitor includes a sensor with a radiation transmitter and a radiation receiver to acquire the heart rate data,
   wherein the sensor is external to the frame,
   wherein the heart-rate monitor includes at least one electrical conductor electrically coupling the sensor to the electronics of the heart-rate monitor embedded in the frame,
   wherein the sensor is incorporated in a clip connected to one end of the electrical connector,
   wherein to acquire the heart rate data, the clip clips onto a part of the body of the user, and at least a portion of the radiation from the transmitter transmits through at least a portion of the body part to be received by the receiver, and
   wherein the radiation includes infrared radiation.

3. A pair of glasses as recited in claim 2, wherein the part of the body is a part of an ear of the user.

4. A pair of glasses as recited in claim 2, wherein the electrical conductor is inside an adjustable mechanical arm.

5. A pair of glasses as recited in claim 2, wherein the electrical conductor is inside a malleable semi-rigid cable.

6. A pair of glasses as recited in claim 1,
wherein the heart-rate monitor includes a sensor with a radiation transmitter and a radiation receiver to acquire the heart rate data,
wherein to measure the heart rate, at least a portion of the radiation from the transmitter is reflected by at least a part of the body of the user, to be received by the radiation receiver, and
wherein the radiation includes infrared radiation.

7. A pair of glasses as recited in claim 1,
wherein the heart-rate monitor includes a sensor with a radiation transmitter and a radiation receiver to acquire the heart rate data,
wherein to acquire the heart rate data at least a portion of the radiation from the transmitter is reflected by at least a part of the body of the user and then received by the radiation receiver,
wherein the frame includes at least one nose pad, and
wherein the sensor is embedded in the nose pad.

8. A pair of glasses as recited in claim 7,
wherein the frame includes electronic circuitry to process outputs from the sensor,
wherein at least a portion of the electronic circuitry configured to process sensor outputs is not at the nose pad, and
wherein the electronic circuitry configured to process sensor outputs is electrically coupled to the sensor via at least one electrical conductor embedded in the frame.

9. A pair of glasses as recited in claim 1, wherein said pair of classes further comprises:
wireless circuitry embedded in the frame and configured to allow wireless transmission of information regarding the acquired heart rate data and/or the user exercise information to at least one other electronic device.

10. A pair of glasses as recited in claim 9, wherein said wireless circuitry is configured to wirelessly transmit signals regarding the acquired heart rate data of the user and/or the user exercise information to a portable or handheld electronic device.

11. A pair of glasses as recited in claim 9, wherein said wireless circuitry is configured to wirelessly transmit signals regarding the acquired heart rate data of the user and/or the user exercise information to an electronic device that is designed to be stationary.

12. A pair of glasses as recited in claim 9, wherein said wireless circuitry is configured to wirelessly transmit signals regarding the acquired heart rate data of the user and the user exercise information to the at least one other electronic device.

13. A pair of glasses as recited in claim 1, wherein said audio output device is a speaker, and wherein the speaker is configured to output music or an exercise program.

14. A pair of glasses as recited in claim 13, wherein the speed of the music depends on an exercise program for the user.

15. A pair of glasses as recited in claim 13, wherein the speed of the music depends on the measured heart rate of the user.

16. A pair of glasses as recited in claim 13, wherein the speaker plays a song that is selected to train the user physically.

17. A pair of glasses as recited in claim 1, wherein the heart rate information is used to calculate calories burnt by the user over a duration of time.

18. A pair of glasses as recited in claim 1, wherein said pair of glasses further comprises a temperature sensor configured to acquire temperature data pertaining to the temperature of the user, and wherein at least a portion of the temperature sensor is embedded in the frame.

19. A pair of glasses as recited in claim 1,
wherein a signal is generated if the user's heart best is beyond a predetermined threshold to provide an alert.

20. A pair of glasses as recited in claim 1, wherein the heart-rate monitor includes a radiation transmitter and a radiation receiver to acquire the heart rate data.

21. A pair of glasses as recited in claim 1, wherein said audio output system is configured to output audio signals comprising heart rate information and exercise information.

22. A pair of glasses as recited in claim 1, wherein said audio output system comprises a speaker.

23. An electronic apparatus that is configured to be worn by a user In the vicinity of the user's head comprising:
a heart-rate monitor with at least a portion of the heart-rate monitor being embedded in the apparatus, the heart-rate monitor being configured to measure heart rate data pertaining to the heart rate of the user;
an electronic device with at least a portion of the electronic device being embedded In the apparatus and configured to acquire user exercise data; and
wireless circuitry embedded in the apparatus and configured to allow wireless transmission of signals pertaining to the measured heart rate data and the user exercise data to at least one other electronic device, and
wherein the heart-rate monitor includes a radiation transmitter and a radiation receiver to measure the heart beat data pertaining to the heart rate of the user.

24. An electronic apparatus as recited in claim 23, wherein the apparatus is selected from a list consisting of a hat, a swimming cap, and a pair of goggles.

25. An electronic apparatus as recited in claim 23, wherein the radiation transmitter and the radiation receiver are embedded at a part of the apparatus that is designed to press against a part of the user's head when the apparatus is worn.

26. An electronic apparatus that is configured to be worn by a user in the vicinity of the users head comprising:
at least one speaker configured to provide audible sound to the user;
a nose pad;
an electronic device with at least a portion of the electronic device being embedded in the apparatus and configured to acquire user exercise data; and
a monitor that is configured to measure a physical condition of the user, with at least a portion of the monitor being embedded in the nose pad,
wherein the monitor is configured to measure the physical condition of the user of the apparatus,
wherein to measure the physical condition of the user, at least a portion of the nose pad is configured to contact with the nose of the user, and
wherein an audio alert is provided to the user of the apparatus via the at least one speaker if the physical condition measured or the user exercise data is beyond a corresponding threshold.

* * * * *

UNITED STATES PATENT AND TRADEMARK OFFICE
CERTIFICATE OF CORRECTION

Page 1 of 3

PATENT NO. : 7,677,723 B2
APPLICATION NO. : 11/650626
DATED : March 16, 2010
INVENTOR(S) : Howell et al.

It is certified that error appears in the above-identified patent and that said Letters Patent is hereby corrected as shown below:

On the Title Page:
Item (56) References Cited U.S. Patent Documents:
"2,794,085 A    5/1957    De Angells"
should be --2,794,085 A    5/1957    De Angelis--.

On Page 2, Item (56) U.S. Patent Documents:
"5,510,981 A    4/1996    Berger et al."
should be --5,510,961 A    4/1996    Peng--.

"7,376,238 B1    5/2009    Rivas et al."
should be --7,376,238 B1    5/2008    Rivas et al.--.

"7,429,985 B2    9/2008    Kimura et al."
should be --7,429,965 B2    9/2008    Weiner--.

"2003/0062046 A1    4/2003    Weismann"
should be --2003/0062046 A1    4/2003    Wiesmann et al.--.

Please insert --2003/0083591 A1    5/2003    Edwards et al.--.

Please insert --2006/0132382 A1    6/2006    Jannard--.

On Page 3, Item (56) under Other Publications:
""Motorola and Oakley Introduce First Bluetooth Sunglasses-Cutting Edge RAZRWIre Line Offers Consumers On-The-Go Connections", Motorola Mediacenter-Press Release, Feb. 14, 2005, pp. 1-2."
should be --"Motorola and Oakley Introduce First Bluetooth Sunglasses-Cutting Edge RAZRWire Line Offers Consumers On-The-Go Connections", Motorola Mediacenter-Press Release, Feb. 14, 2005, pp. 1-2.--.

Signed and Sealed this
Eighth Day of September, 2015

Michelle K. Lee
*Director of the United States Patent and Trademark Office*

CERTIFICATE OF CORRECTION (continued)
U.S. Pat. No. 7,677,723 B2

""Oakley Thump: Sunglasses Meet MP3 Player", with Image, http://news.designtechnica.com/article4665.html, Jul. 13, 2004."
should be --"Oakley Thump: Sunglasses Meet MP3 Player", with image, http://news.designtechnica.com/article4665.html, Jul. 13, 2004.--.

""Personal UV monitor," OptIcs.org, http://optics.org/articles/news/6/6/7/1 (downloaded Dec. 20, 2003), Jun. 9, 2000, pp. 1-2."
should be --"Personal UV monitor," Optics.org, http://optics.org/articles/news/6/6/7/1 (downloaded Dec. 20, 2003), Jun. 9, 2000, pp. 1-2.--.

""SafeSun Personal UV Meter", Introduction, Optlx Tech Inc., http://www.safesun.com, downloaded Feb. 5, 2004, pp. 1-2."
should be --"SafeSun Personal UV Meter", Introduction, Optix Tech Inc., http://www.safesun.com, downloaded Feb. 5, 2004, pp. 1-2.--.

"Alps Spectable, Air Conduction Glass, Bone Conduction Glass, htt;://www.alps-Inter.com/spec.htm, downloaded Dec. 10, 2003, pp. 1-2."
should be --Alps Spectable, Air Conduction Glass, Bone Conduction Glass, http://www.alps-inter.com/spec.htm, downloaded Dec. 10, 2003, pp. 1-2.--.

"Bone Conduction Headgear HG16 Series, "Voiceducer", http://www.ternco-j.co.jp/html/English/HG16.html, downloaded Dec. 10, 2003, pp. 1-3."
should be --Bone Conduction Headgear HG16 Series, "Voiceducer", http://www.temco-j.co.jp/html/English/HG16.html, downloaded Dec. 10, 2003, pp. 1-3.--.

"Clifford, Michelle, A., "Acccelerometers Jump into the Consumer Goods Marker", Sensors Online, http://sensormag.com, Aug. 2004."
should be --Clifford, Michelle, A., "Accelerometers Jump into the Consumer Goods Market", Sensors Online, http://sensormag.com, Aug. 2004.--.

"Grobert, Sam, "Digit-Sizing Your Computer Data", News Article, Sep. 2004, p. 1."
should be --Grobart, Sam, "Digit-Sizing Your Computer Data", News Article, Sep. 2004, p. 1.--.

On Page 4, Item (56) under Other Publications:
"Mio, PhyslCal, http://www.gophysical.com/, downloaded Jan. 27, 2004, 5 pages."
should be --Mio, PhysiCal, http://www.gophysical.com/, downloaded Jan. 27, 2004, 5 pages.--.

"Top Silicon Pin Photodiode, PD93-21C, Technical Data Sheet, Everlight Electronics Co., Ltd., 2004, pp. 1-9."
should be --Top Silicon PIN Photodiode, PD93-21C, Technical Data Sheet, Everlight Electronics Co., Ltd., 2004, pp. 1-9.--.

CERTIFICATE OF CORRECTION (continued)
U.S. Pat. No. 7,677,723 B2

"UV-Smart, UVA/B Monitor, Model EC-960-PW, Instruction Manual, Tanlta Corporation of America, Inc., downloaded Nov. 16, 2001."
should be --UV-Smart, UVA/B Monitor, Model EC-960-PW, Instruction Manual, Tanita Corporation of America, Inc., downloaded Nov. 16, 2001.--.

In the Specification:
Column 1, line 20, "filed Dec. 6, 2003, and entitled"
should be --filed Dec. 8, 2003, and entitled--.

Column 1, line 38, "hereby Incorporated herein by"
should be --hereby incorporated herein by--.

In the Claims:
Column 17, line 34 (claim 9), "of classes further"
should be --of glasses further--.

Column 18, line 10 (claim 19), "heart best is"
should be --heart beat is--.

Column 18, line 44 (claim 26), "users head"
should be --user's head--.

UNITED STATES PATENT AND TRADEMARK OFFICE
CERTIFICATE OF CORRECTION

PATENT NO. : 7,677,723 B2
APPLICATION NO. : 11/650626
DATED : March 16, 2010
INVENTOR(S) : Howell et al.

It is certified that error appears in the above-identified patent and that said Letters Patent is hereby corrected as shown below:

In the Specification
Column 8, lines 49-50, "described on stabling the wire"
should be --described on stabilizing the wire--.

Signed and Sealed this
Seventh Day of June, 2016

Michelle K. Lee
*Director of the United States Patent and Trademark Office*